(12) United States Patent
Claycamp

(10) Patent No.: US 9,079,184 B2
(45) Date of Patent: Jul. 14, 2015

(54) GRAIN FRACTION ENDOSPERM RECOVERY SYSTEM

(75) Inventor: Daniel L. Claycamp, West Frankfort, IL (US)

(73) Assignee: MOR Technology, LLC, Metropolis, IL (US)

( * ) Notice: Subject to any disclaimer, the term of this patent is extended or adjusted under 35 U.S.C. 154(b) by 521 days.

(21) Appl. No.: 13/579,250

(22) PCT Filed: Feb. 15, 2011

(86) PCT No.: PCT/US2011/000277
§ 371 (c)(1),
(2), (4) Date: Aug. 15, 2012

(87) PCT Pub. No.: WO2011/100073
PCT Pub. Date: Aug. 18, 2011

(65) Prior Publication Data
US 2012/0312905 A1    Dec. 13, 2012

Related U.S. Application Data

(60) Provisional application No. 61/304,729, filed on Feb. 15, 2010.

(51) Int. Cl.
*B03B 5/28* (2006.01)
*B02C 9/04* (2006.01)
*A23L 1/10* (2006.01)
*B02C 23/08* (2006.01)
*C12P 7/06* (2006.01)

(52) U.S. Cl.
CPC ............... *B02C 9/04* (2013.01); *A23L 1/1016* (2013.01); *A23L 1/1025* (2013.01); *B02C 23/08* (2013.01); *C12P 7/06* (2013.01); *Y02E 50/17* (2013.01)

(58) Field of Classification Search
CPC .............. B04B 1/20; B02C 3/08; B02C 9/042
USPC ...................................... 209/3, 724
See application file for complete search history.

(56) References Cited

U.S. PATENT DOCUMENTS 2,122,084 A * 6/1938 Brown et al. ............... 127/68
4,154,728 A   5/1979 Oughton
(Continued)

FOREIGN PATENT DOCUMENTS

WO   WO 2002/067698       9/2002
WO   WO 2005/074625 A2    8/2005
WO   WO 2005/074625 A3    8/2005

OTHER PUBLICATIONS

U.S. Appl. No. 61/304,729, filed Feb. 15, 2010.
(Continued)

*Primary Examiner* — Terrell Matthews
(74) *Attorney, Agent, or Firm* — Craig R. Miles; CR Miles P.C.

(57) ABSTRACT

Generally, a dry-wet grain fractionation system which provides a dry mill process (26) for the production of grain fractions (14) (15) (16) and a wet mill process (18) for the production of purified bran (19), endosperm (20) and germ (21) from the mixture of grain particles in a grain fraction (14) (15) or (16) or combinations thereof. Specifically, a dry-wet grain fractionation system for production of corn germ (21) having increased protein and oil content and an endosperm (20) having increased starch and sugar content.

20 Claims, 8 Drawing Sheets

(56) References Cited

U.S. PATENT DOCUMENTS

| | | | |
|---|---|---|---|
| 4,171,383 | A | 10/1979 | Chwalek et al. |
| 4,181,748 | A | 1/1980 | Chwalek et al. |
| 4,211,695 | A | 7/1980 | Oughton |
| 4,435,429 | A | 3/1984 | Burrows et al. |
| 6,939,294 | B2 | 9/2005 | Abe |
| 7,104,479 | B1 | 9/2006 | Griebat et al. |
| 7,152,818 | B2 | 12/2006 | Strissel et al. |
| 7,709,033 | B2 | 5/2010 | Kvist et al. |
| 8,409,639 | B2 * | 4/2013 | Lewis et al. ............ 426/11 |
| 2004/0197449 | A1 | 10/2004 | Van Thorre |
| 2005/0089602 | A1 | 4/2005 | Kvist et al. |
| 2005/0095331 | A1 | 5/2005 | Van Thorre |
| 2005/0118693 | A1 | 6/2005 | Thorre |
| 2005/0175734 | A1 * | 8/2005 | Angelini et al. ............ 426/41 |
| 2008/0279983 | A1 | 11/2008 | Lohrmann et al. |
| 2015/0028139 | A1 * | 1/2015 | Bihn ............................ 241/7 |

OTHER PUBLICATIONS

International Patent Corporation Treaty Patent Application No. PCT/US2011/000277, filed Feb. 15, 2011.
U.S. Appl. No. 11/268,146, filed Nov. 7, 2005.
U.S. Appl. No. 11/726,255, filed Mar. 21, 2007.
U.S. Appl. No. 12/117,621, filed May 8, 2008.
Patent Cooperation Treaty Application No. PCT/US2006/045193.
Arterburn. The Sizing and Selection of Hydrocyclones, FLSmidth-Krebs, POB, Landenberg, Pennsylvania, USA (2008).
Freeman. Quality Factors Affecting Value of Corn for Wet Milling, Trans. ASAE 16:671-678, 682 (1973).
Wang, et al. Effect of Broken Corn Levels on Water Absorption and Steepwater Characteristics, Cereal Chem. 77:525-528 (2000).
Wang, et al. Effect of Broken Corn Levels on Water Absorbtion and Steepwater Characteristics, Cereal Chem. 77:525-528 (2000).

* cited by examiner

GRAIN FRACTION ENDOSPERM RECOVERY SYSTEM

This application is the United States National Stage of International Patent Corporation Treaty Patent Application No. PCT/US2011/000277, filed Feb. 15, 2011, which claims the benefit of U.S. Provisional Patent Application No. 61/304,729, filed Feb. 15, 2010, each hereby incorporated by reference herein.

I. TECHNICAL FIELD

Generally, a dry-wet grain fractionation system which can be used to produce grain fractions from a mixture of milled grain particles. Specifically, a dry-wet grain fractionation system for generating a germ fraction having increased protein and oil content and endosperm fraction having increased starch and sugar content.

II. BACKGROUND

As shown in FIG. 1, certain conventional corn mill processes (1) may mill an amount of whole corn (2) into a mixture of corn particles (3) (referred to hereinafter as "milled corn") which may include particles of corn bran (19), corn endosperm (20) and corn germ (21). Certain of the particles of corn germ (21) and corn bran (19) may have bound or have associated particles of corn endosperm (20). The milled corn (3) can be transferred to an ethanol production process (4) which includes the conventional steps of fermentation, distillation, and dehydration to generate an amount of ethanol (5). In the fermentation step, the milled corn (3) may be combined with an amount of water and an amount of alpha-amylase (or other enzyme capable of liquefying corn starch) to generate a mash in which the starch of the corn endosperm is liquefied. The mash may be held for a period of time at a temperature of between about 77 degrees Celsius ("° C.") (about 170 degrees Fahrenheit ("° F.") and about 100° C. (about 212° F.) to kill bacteria in the mash. The mash may then be held at a temperature of between about 32° C. (about 90° F.) and about 38° C. (about 100° F.) for a period of time sufficient to achieve a desired level of liquefaction of the starch. An amount of gluco-amylase (or other enzyme capable of generating fermentable sugars from the liquefied starch) added to the mash converts the liquefied starch to fermentable sugars, such as dextrose, in a process referred to as saccharification. Yeast can then be added to the mash and the mash held at a temperature of between about 29° C. (about 85° F.) and about 32° C. (about 90° F.) to convert the sugars to an amount of ethanol (5) and an amount of carbon dioxide (6) (or "CO2") along with other volatile organics. The amount of carbon dioxide (6) can be stored or sold in the marketplace. For sale into certain markets or for use in certain applications, the amount of carbon dioxide (6) can be stripped of the other volatile organics and captured as an amount of purified carbon dioxide (9). The fermented mash often referred to as "beer" includes an amount of ethanol (5) in a concentration of about eight percent ("%") to about 20% by weight, other liquids and non-fermentable solids. The amount of ethanol (5) in the beer can be separated and concentrated to about 190 proof by conventional distillation techniques and dehydrated by application to molecular sieve to produce a dehydrated ethanol (5) of about 200 proof. Ethanol (5) of about 200 proof may be combined with up to about five percent denaturant to generate an amount of fuel ethanol (10).

The stillage which remains after distillation of the beer can comprise an amount of liquid typically referred to as "thin stillage" and an amount of remaining solids typically referred to as the "distillers grains". The thin stillage can be separated from the distillers grains (for example by centrifugation). The distillers grains can be dried by evaporation of the remaining thin stillage to produce "dried distillers grains" ("DDG") (7). The thin stillage can be concentrated by evaporation of water to generate a syrup containing about thirty percent solids (also referred to as "condensed distiller soluble"). The syrup can be recombined with the dried distillers grains (7) to generate an amount of distillers dried grain with solubles (8) ("DDGS"). The DDGS (8) can be sold as animal feed.

Even though there is an increasing demand for fuel ethanol (10) worldwide and an increasing amount of research in ethanol production, there remain substantial unresolved problems with respect to conventional corn mill processes (1) for ethanol (5) production.

A first substantial problem with conventional corn mill processes (1) for ethanol (5) production can be that milled corn (3) introduced into the ethanol production process (4) which includes corn bran (19), corn endosperm (20) and corn germ (21) requires an amount of thermal energy (11) (or energy Btus or Btus) to complete the steps of fermentation, distillation and dehydration, and by-product handling. To generate about a gallon of fuel ethanol (10), and a corresponding amount of DDGS (8) and carbon dioxide (6) the ethanol production process (4) utilizing milled corn (3) consumes an amount of thermal energy (11) of between about 20,000 British thermal units (hereinafter "Btu") and about 35,000 Btu (the term "about" as used herein means greater or lesser than the value or range of values stated by 10 percent, but not does not limit any value or range of values to this broader definition and each value or range of values preceded by the term "about" also includes in the alternative the stated absolute value or range of values). This amount of thermal energy (11) is typically generated by burning a corresponding amount of fossil fuel (12) such as oil, coal oil, coal, natural gas, or the like.

Inclusion of an amount of non-fermentable biomass or substantially non-fermentable biomass, such as corn bran (19) or corn germ (21), into the ethanol production process (4) requires allocation of an amount of thermal energy (11) to process the amount of non-fermentable biomass; however, this amount of non-fermentable biomass or substantially non-fermentable biomass does not produce any or produces very little ethanol (5) which increases the amount of thermal energy (11) used per unit of ethanol (5) produced as compared to an ethanol production process (4) in which only the fermentable corn endosperm (20) is processed. Because the corn bran (19) and corn germ (21) represent about 17% by weight of the milled corn (3), if the corn bran (19) and the corn germ (21) can be removed from the ethanol production process (4), than the amount of thermal energy (11) consumed by the ethanol production process (4) per unit of ethanol (4) produced may be substantially reduced.

A second substantial problem with the conventional corn mill process (1) for ethanol production (4) can be that milled corn (3) introduced into the ethanol production process (4) which includes non-fermentable biomass or substantially non-fermentable biomass requires allocation of an amount of fermenter capacity to biomass which does not produce any or produces very little ethanol (5). If the corn bran (19) and the corn germ (21) can be removed from the ethanol production process (4), then the corresponding amount of fermenter capacity freed up could be utilized to process additional fermentable biomass.

A third substantial problem with the conventional corn mill process (1) for ethanol production can be that milled corn (3)

introduced into the ethanol production process (4) which includes non-fermentable biomass or substantially non-fermentable biomass increases the amount of "distillers grains" produced per unit of ethanol (5) produced. The distillers grains must be dried as above-described to produce dried distiller grains ("DDG") (7) or dried distillers grains with solubles ("DDGS") (8). The drying of "distillers grains" can be the single largest point of energy (11) consumption in the ethanol production process (4). If the corn bran (19) and the corn germ (21) can be removed from the ethanol production process (4), then a corresponding reduction in the amount "distillers grains" can be achieved with a corresponding reduction in the amount of thermal energy (11) utilized to produce DDG (7) per unit of ethanol (5) produced.

A fourth substantial problem with conventional corn mill processes (1) for ethanol production (4) can be that the market for conventional DDG (7) by products may become saturated as the number of ethanol production facilities increases. Conventional DDG (7) includes corn bran (19). As the amount of corn bran (19) increases in the DDG (7) the percent protein by weight decreases. As the percent protein by weight of the DDG (7) decreases the value of the DDG (7) or DDGS (8) as a feed may also decrease. Additionally, inclusion of corn bran (19) in the DDG (7) increase the fiber content of the DDG (7) which can make the DDG (7) unacceptable as a feed for poultry, fish and pet food.

Now referring primarily to FIG. 2, an alternative to the conventional corn mill process (1) can be a dry corn mill process (13) which facilitates isolation of a corn bran fraction (15), a corn germ fraction (16), and a corn endosperm fraction (14). The corn endosperm fraction (14) generated from the conventional dry corn mill process (13) can be introduced into an ethanol production process (4) above-described to in part address certain of the above-identified problems. However, because the primary function of the conventional dry corn mill process (13) is to facilitate the production of a lowered-fat grit or meal for the production of food products such as cereal, table grits or the like, the conventional dry corn mill process shown in FIG. 2 (13) including hardware and methods of utilizing the hardware have not been developed to produce a corn endosperm fraction (14) for introduction into an ethanol production process (4). Now referring to FIG. 2 and Table 1, conventional dry milling process (13) for whole corn (2) can generate a corn germ fraction (16) or a corn bran fraction (15) which still includes a substantial amount of corn endosperm (20) (reported out as "starch" in Table 5). However, loss of corn endosperm (20) to the corn germ fraction (16) or the corn bran fraction (15) solely to increase purity of the corn endosperm fraction (14) in the context of an ethanol production process (4) can result in significant economic losses.

Another substantial problem with the dry corn mill process (13) can be that the resulting corn germ fraction (16) may not contain sufficient corn oil (22) on a dry matter basis to economically enter conventional corn oil extraction processes (23). Corn germ (21) which enters conventional corn oil (22) extraction processes is typically greater than 30% corn oil (22) on a dry matter basis ("dmb"). Currently, conventional dry corn mill processes (13) produce a corn germ fraction (16) having corn oil (22) on a dmb in a range of about 15% and about 25%.

Another substantial problem with dry corn mill processes (13) can be that the resulting corn germ fraction (16) does not have a desired protein dispersibility index ("PPI"). The PDI is a measure of the total protein (24) in the corn germ fraction (16) on a dmb which can be extracted into water.

Now referring primarily to FIG. 3, the use of conventional wet corn mill process (17) has been used to address certain problems associated with the conventional dry mill process (13). In the conventional wet mill process (17), whole kernel corn (2) enters a wet mill process (18) in which the whole corn (2) enters a steep liquid (25) (typically water which can further include sulfur dioxide) for a period of between 24 and 36 hours to soften the constituent parts of the kernel of whole corn (2). The softened kernel of whole corn (2) can be ground to free the corn germ (21) from the corn bran (19) and the corn endosperm (20). Because the corn germ (21), the corn bran (19) and the corn endosperm (20) of softened whole corn (2) break away from one another more cleanly when ground, the purity of the separated corn germ fraction (16), corn bran fraction (15) and corn endosperm fraction (14) may have an increased purity on a dmb as compared to the conventional dry corn mill process (13). The corn endosperm fraction (14) can be introduced into a conventional ethanol production process (4) for the production of ethanol (5) and fuel ethanol (10), as above described.

A substantial problem with conventional wet milling process (17) may be that the quality of the whole corn (2) introduced into the conventional wet milling process (17) has to be greater than that introduced into a conventional dry milling process (13). Freeman, J. E., *Quality Factors Affecting Value of Corn for Wet Milling, Trans. ASAE* 16:671-678, 682 (1973); and Wang, D. and Eckhoff, S. R., *Effect of Broken Corn Levels on Water Absorbtion and Steepwater Characteristics, Cereal Chem.* 77:525-528 (2000), each incorporated by reference herein. Broken or cracked pieces of corn (24) mixed into the whole corn (2) must be removed by screening before the proceeding with conventional wet milling process (17) as these broken pieces of corn (24) slough off starch, sugars, and protein which enter the steep water (18) and cause gelling during evaporation of the steep water (18). Also, the increased viscosity of the steep water (18) may restrict water flow through the steeps and screens. Additionally, conventional corn wet milling consumes a great amount of water and energy generate conventional corn fractions (14) (15) (16).

The inventive dry-wet grain fractionation system addresses each of the foregoing problems of the conventional dry corn mill process and the conventional wet corn mill process.

III. DISCLOSURE OF INVENTION

Accordingly, a broad object of the invention can be to provide a dry-wet grain fractionation system which operates to isolate a bran fraction, a germ fraction, and an endosperm fraction which have a greater purity coupled with a greater yield as compared to conventional dry mill or wet mill processes.

Another broad object of the invention can be to provide a wet milling process that receives less than 15% wt./wt. of the entire grain kernel as compared to conventional wet milling processes which process whole grain kernels. Wet processing of grain fractions by embodiments of the invention which result from the above described conventional dry mill processes or other conventional or inventive dry mill processes confers the advantages of wet mill processing of a substantially reduced weight of material which can achieve an overall cost savings, while producing a similar or better quality of germ, endosperm and bran.

Another broad object of the invention is to provide a dry-wet corn fractionation system which can wet process the corn bran fraction, the corn germ fraction, and the corn endosperm fraction produced by the conventional dry corn mill process without having to use the sulfur dioxide steeping process of the conventional wet mill process.

Another broad object of the invention can be to provide a corn endosperm fraction having a starch content on a dmb in a range of about 60% to about 65% with a crude fat content on a dmb in the range of about 0.5% and about 1.00%.

Another broad object of the invention can be to provide a corn germ fraction having crude fat content on a dmb in a range of about 30% to about 55%.

Another broad object of the invention can be to couple the corn endosperm fraction produced by the dry-wet mill corn fractionation system to an ethanol production process to decrease thermal energy consumption, increase ethanol production capacity, and produce a high protein dried fractionated corn gluten meal whether independently or in various combinations and permutations.

Naturally, further objects of the invention are disclosed throughout other areas of the specification, drawings, and claims.

IV. BRIEF DESCRIPTION OF THE DRAWINGS

Figure 8:
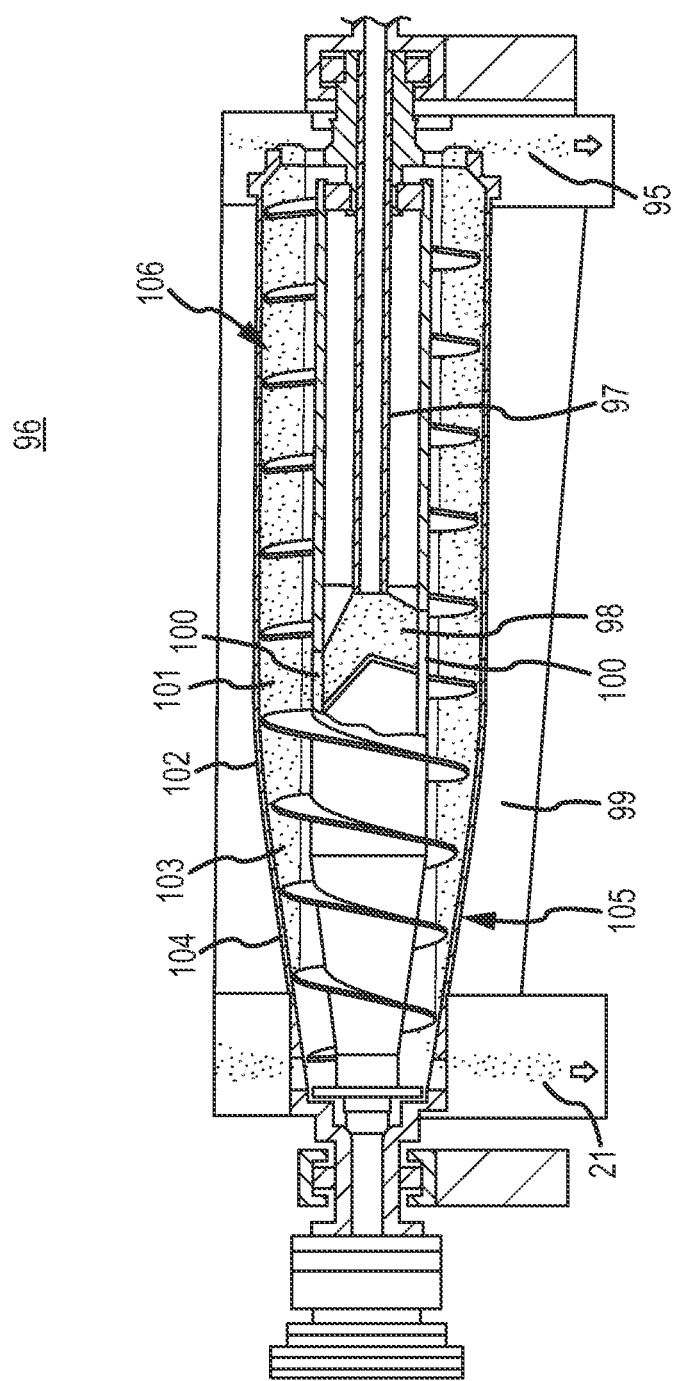

FIG. 8 a cross section view of a particular decanter device which can be utilized in the inventive dry-wet corn fractionation system.

V. MODE(S) FOR CARRYING OUT THE INVENTION

Generally, a dry-wet grain fractionation system which can be used to produce grain fractions from a mixture of milled grain particles. Specifically, a dry-wet grain fractionation system for generating a germ fraction having increased protein and oil content and endosperm fraction having increased starch and sugar content.

Now referring primarily to FIGS. 4 and 5, which together illustrate a particular embodiment of the dry-wet corn fractionation system (26), as further described below. In part, the wet-dry corn fractionation system (26) can include a corn cleaner (27) to receive whole corn (2). One non-limiting example of a corn cleaner (27) moves whole corn (2) along a first sloping deck of having a plurality of holes. Whole corn (2) can pass through the holes onto a second sloping deck thereby removing material larger than a kernel of whole corn (2). The whole corn (2) then moves along a second sloping deck having holes of lesser size then a kernel of whole corn (2) thereby removing material smaller than a kernel of whole corn (2). The corn cleaner (27) can further include a cleaner aspirator (28). Whole corn (2) can pass through the cleaner aspirator (28) (as a non-limiting example a Series E six path unit available from Kice Industries, Inc., 5500 North Mill Heights Drive, Wichita, Kans.) to remove material having lesser density than a kernel of whole corn (2). The corn cleaner (27) can further include a de-stoner (29) which removes materials of greater density than a kernel of whole corn (2). The term "whole corn (2)" as used herein broadly encompasses kernels of corn removed from the cob regardless of the variety or grade and can include kernels of corn which might be unacceptable in a conventional wet milling process (17) because the kernels are broken, split, cracked or fractured. Additionally, it is not intended that the example of a corn cleaner (27) be limited to above-described configuration and any manner of corn cleaning which results in whole corn (2) or parts thereof which are substantially free of other materials can be utilized with the various embodiments of the dry-wet corn fractionation system (23).

Figure 4:
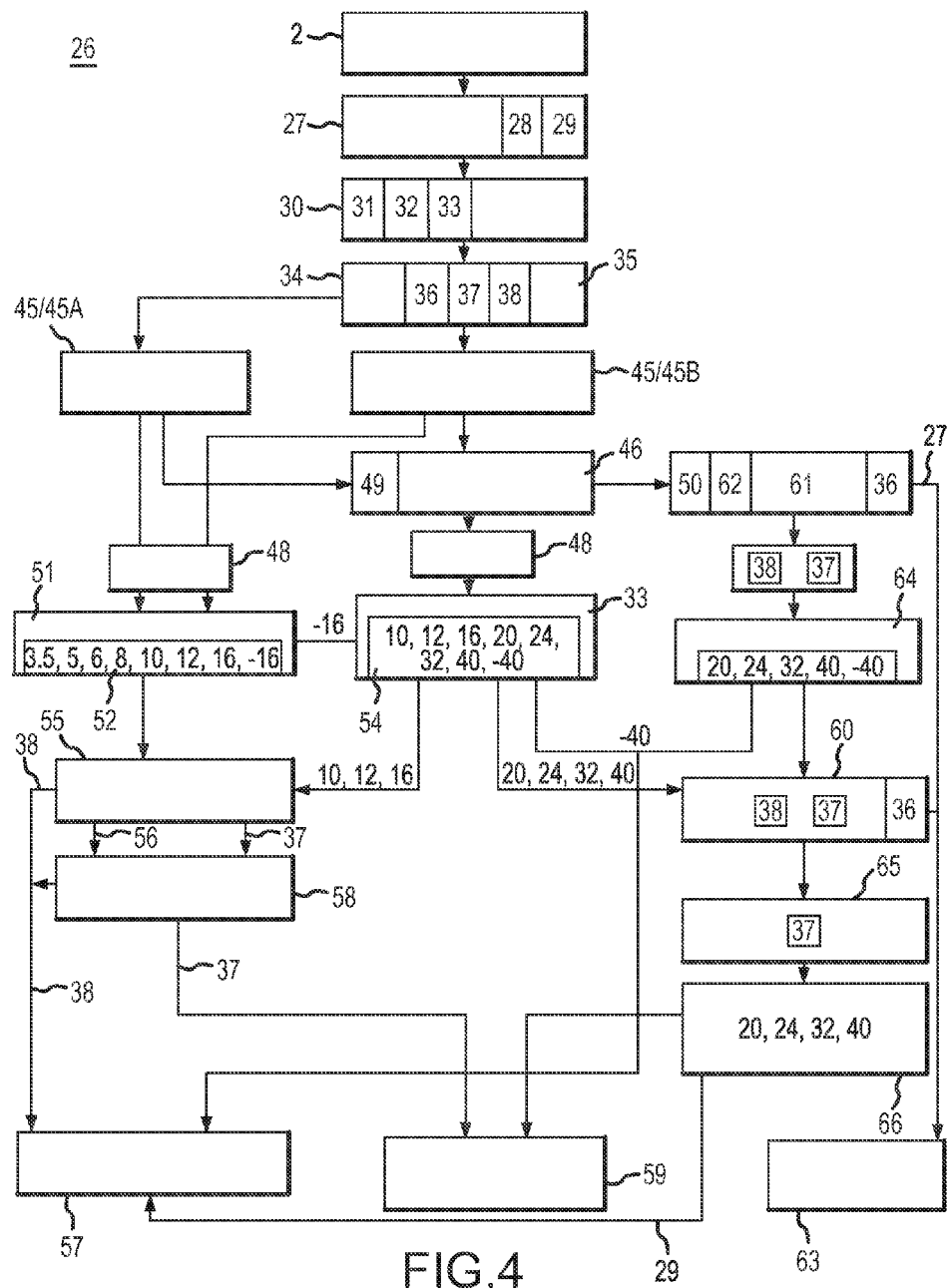
FIG. 4 is a block flow diagram of a particular embodiment of the dry mill process of the inventive dry-wet corn fractionation system.

Now referring primarily to FIG. 4, as to certain embodiments of the inventive dry-wet corn fractionation process (26), the whole corn (2) substantially free of other materials can include a corn temper process (30). The whole corn (2) cleaned of other materials can be transferred by a conveyor (28) (as a non-limiting example a Bi-Mix 30-55/180-22 available from GBS Group S.p.a, Corso Uniti, 7, Padova, Italy). As the whole corn (2) moves up the inclined conveyor (31), water and steam can be introduced to the whole corn (2) and mixed by the conveyor (31) (by paddles, screws, or the like). The whole corn (2) leaves the conveyor (31) and drops into a temper tank (31). The whole corn (2) resides in the temper tank (32) for a duration of time of between about five minutes and fifteen minutes to allow the water to be distributed over the entire kernel of whole corn (2) and absorbed by the bran coat until the bran coat reaches a pre-selected target moisture.

Again referring primarily to FIG. 4, after the corn temper process (30) a plurality of kernels of tempered whole corn (33) can be accepted by a kernel fracture assembly (34) which breaks the tempered whole corn (33) (or whole corn (2) where the corn temper process (30) is omitted) into a plurality of corn particles (32). The plurality of corn particles (35) includes a mixture of a plurality of corn bran particles (36), a plurality of corn germ particles (37) and a plurality of corn endosperm particles (38). Understandably, the definition of a plurality of corn particles (35) also includes certain of the plurality of corn particles (35) which are in various permutations a combination of more than one of corn germ, corn bran, and corn endosperm which require further processing as described below for fractionation into one of a plurality of bran particles (36), a plurality of corn germ particles (37), or corn endosperm particles (38). Numerous and varied kernel fracture assemblies (31) can be utilized to generate the plurality of corn particles (35) having a size distribution or a range of size distributions suitable for use in the dry-wet corn fractionation system (26).

Figure 6A:
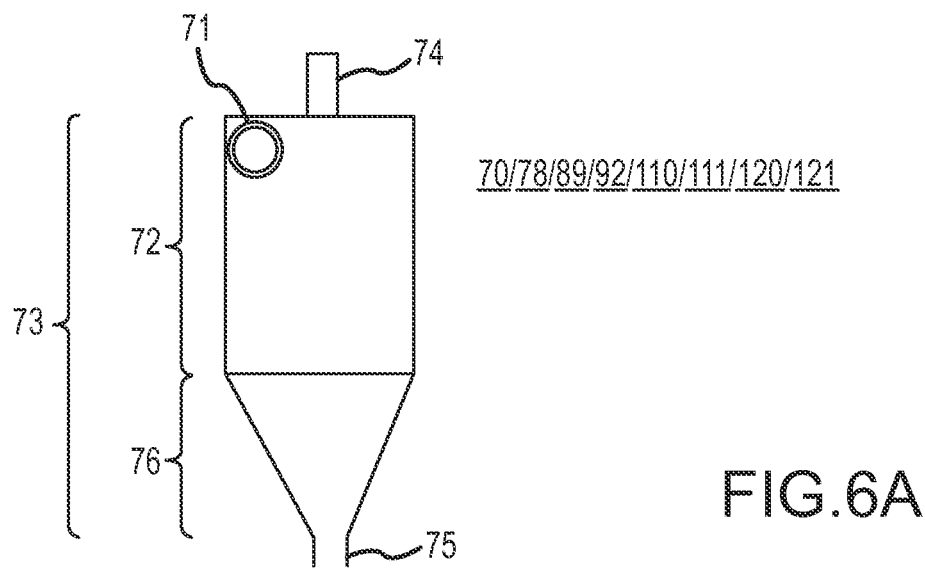
FIG. 6A is a block diagram of a particular embodiment of a centrifugal force separator utilized in a substantially vertical orientation.
Figure 6B:
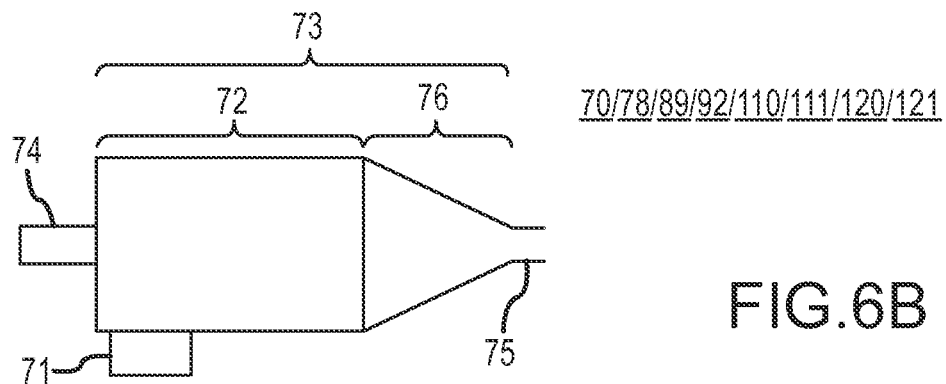
FIG. 6B is a block diagram of a particular embodiment of a centrifugal force separator utilized in a substantially horizontal orientation with the inlet below the cylindrical-conical chamber.
Figure 6C:
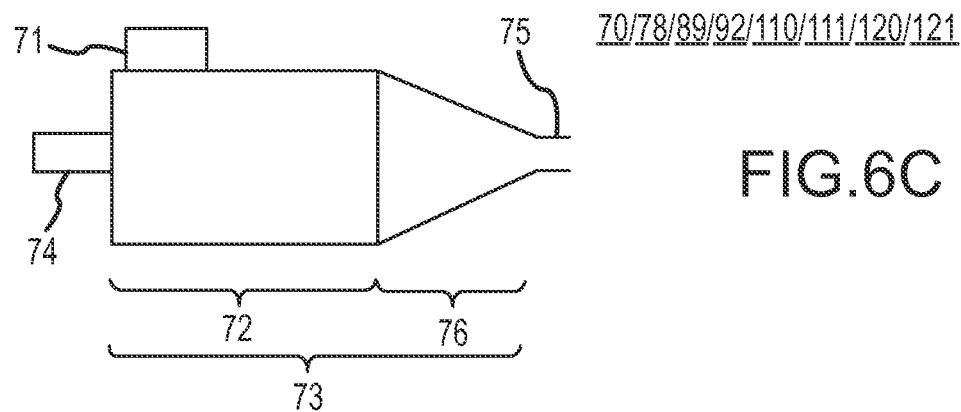
FIG. 6C is a block diagram of a particular embodiment of a centrifugal force separator utilized in a substantially horizontal orientation with the inlet above the cylindrical-conical chamber.

Now referring primarily to FIG. 6, one non-limiting kernel fracture assembly (34) suitable for use in the inventive dry-wet corn fractionation system (26) can be a conventional Satake Maize Degermer, model VBF 10AM-L available from Satake Corporation, 2-30, Saijo, Nishiho-machi, Higashihi-roshia-shi, Hiroshima, Japan, or similar device. As to those embodiments of the inventive dry-wet corn fractionation system (26) which include the Satake Maize Degermer as the kernel fracture assembly (34), the Satake Maize Degermer can be utilized as originally configured or the Satake Maize Degermer, or similar device, can be altered or modified as shown in FIG. 6 to produce the plurality of corn particles (35) with a greater average particle size distribution than can be produced by the conventional Satake Maize Degermer. The conventional slotted screens (not shown) provided with the Satake Maize Degermer above-describe can have a plurality of 0.8 mm slots can be replaced with perforated screens (39) each having a plurality of perforations (40) of about the same number as the conventional slots and each being substantially circular having diameter in the range of between about 5 millimeters ("mm") to about 10 mm with certain embodiments having diameter of between about 6 mm to about 9 mm and with certain embodiments having a diameter of between about 6 mm to about 8 mm. Certain non-limiting embodiments of the perforated screens (39) as shown in FIG. 6 can have a plurality of perforations of be about 7 mm. However, the desired size distribution of the plurality of corn particles (35) may be obtained utilizing other perforation configurations and the invention is not limited solely to substantially circular perforations but to any configuration of perforation which can yield a particle size distribution suitable for use with in dry-wet corn fractionation system (26). The plurality of perforations (40) can be located at the same or similar locations of the prior conventional slots, however, the invention is not so limited and the location or placement pattern of the plurality of perforations (40) can be any location or placement which yields a particle size distribution of the plurality of corn particles (35) suitable for use in the inventive dry-wet corn fractionation system (26).

Additionally, the conventional 4 mm breaker bars (often referred to as "clickers") can be replaced with modified breaker bars (41) of between about 6 mm to about 10 mm at substantially the same locations as the conventional clickers, or replacing both. Again, based on the configuration and placement of the plurality of perforations (40), embodiments of the invention can utilize unmodified clickers (41), or modified breaker bars to generate the particle size distribution of the plurality of particles (35) suitable for use with the dry-wet mill fractionation system (26). Alternately, as to certain embodiments the clickers (41) can be modified and the plurality of perforations (40) configured to the extent necessary to generate a particle size distribution suitable for use in the dry-wet mill fractionation system (26). One non-limiting embodiment of the invention adjusts both the plurality of perforations (40) and the modified breaker bars (41) can be utilized to produce the particle size distribution described herein below.

With respect to the operation of the Satake Maize Degermer, the plurality of kernels of tempered whole corn (33) can enter the bottom of a substantially vertical cylinder (42) and become located between the surface of a rotating drum (43) and the inside walls (44) of the steel cylinder (42) to become fractured by kernel on steel impact and by kernel on kernel impact into the plurality of corn particles (35). A part of the plurality of corn particles (35) can pass through the perforations in the walls of the steel cylinder (referred to as the "throughs"). The remaining plurality of corn particles (35) pass over the top of the steel cylinder (referred to as the "tails").

By modifying the Satake VBF Maize Degermer as above-described, the size distribution of the plurality of corn particles (35) generated substantially changes with respect to the "tailstock" and the "through stock". Referring first to Table 1 below fracturing of a plurality of tempered whole corn (33) with a conventional Satake VBF can result in amount of "tailstock" of about 73 percent by weight of the tempered whole corn (30) introduced into the Satake VBF Degermer. The size distribution of the "tailstock" held by a 3.5 wire, a 4 wire, a 5 wire, a 6 wire, an 8 wire, or a 10 wire sifter and the amount passing through the 10 wire sifter to the pan are shown as percents by weight of the total weight of the tempered corn kernels (30) introduced into the Satake VBF Maize Degermer and as a percent of the total weight of the tailstock generated. Similarly, as shown by Table 2 fracturing of a tempered whole corn (33) results in a conventional amount of "throughstock" of about 22 percent by weight of the plurality of corn kernels (24) introduced into the Satake VBF Degermer. The size distribution of the "throughstock" held by a 6 wire, a 4 wire, a 10 wire, a 14 wire, an 18 wire, a 24 wire, and a 40 wire sifter, and passing through the 40 wire sifter to the pan are shown respectively as a percent by weight of the total weight of the tempered whole corn kernels (30) introduced into the Satake Degermer and as a percent total weight of the throughstock generated.

Now referring primarily to Tables 1-4 comparing the size distribution of the plurality of particles (35) conventionally generated by an unmodified Satake VBF Maize Degermer to the size distribution of the plurality of particles (35) generated by the non-limiting examples of the modified Satake VBF Maize Degermer as above described, it can be understood that the size distribution for the "tailstock" and the "through-stock" generated by the modified Satake VBF Maize Degermer falls in a narrower range of particle size with lesser of the plurality of corn particles (35) held by the 3.5 wire screen (typically re-fractured) and with a reduction in the plurality of particles (35) having a size lesser than can be held by a 10 wire screen. As such, the vast majority of the plurality of particles (35) produced by the corn fracture assembly (34) in the form of the modified Satake VBF Degermer can fall in the range of −3.5 wire (falling through a 3.5 wire screen) and +10 wire (retained by a 10 wire screen). As compared to the conventional range of −3.5 wire and +40. Note, that the amount of −10 particles (falling through a 10 wire screen) for the tailstock and the through stock combined is reduced by about 15 percent to about 25 percent over the conventional corn fracture process. Also the amount of fines −40 wire (falling through a 40 wire screen) produced by the inventive corn fracture assembly is substantially reduced. Reduction in the amount fines significantly lower water content of the plurality of corn particles (35) and allows subsequent steps in the inventive dry-wet corn fractionation system (26) to operate without or with a reduced aggregation of the plurality of corn particles (35).

TABLE 1

Conventional Corn Particle Size Distribution Of Tailstock Generated By A Conventional Satake Maize Degermer.

| | Wires/In. | % Retained Of Total Whole Corn | % Total Retained Of Tailstock |
|---|---|---|---|
| Sifted Tails | | | 72.98% |
| | 3.5 | 31.77% | 23.19% |
| | 4 | 7.75% | 5.66% |
| | 5 | 22.38% | 16.33% |

TABLE 1-continued

Conventional Corn Particle Size Distribution Of Tailstock
Generated By A Conventional Satake Maize Degermer.

| Wires/In. | % Retained Of Total Whole Corn | % Total Retained Of Tailstock |
|---|---|---|
| 6 | 15.28% | 11.15% |
| 8 | 10.92% | 7.97% |
| 10 | 5.35% | 3.90% |
| pan (−10) | 6.55% | 4.78% |
| Total | 100.00% | 72.98% |

TABLE 2

Conventional Corn Particle Size Distribution Of Throughstock
Generated By A Conventional Satake Maize Degermer.

| Wires/In. | % Retained Of Total Whole Corn | % Total Retained Of Tailstock |
|---|---|---|
| Sifted Throughs | | 21.51% |
| 6 | 0.00% | 0.00% |
| 10 | 0.57% | 0.12% |
| 14 | 1.00% | 0.22% |
| 18 | 8.14% | 1.75% |
| 24 | 15.14% | 3.26% |
| 40 | 28.43% | 6.11% |
| pan (−40) | 46.71% | 10.05% |
| Total | 100.00% | 21.51% |

TABLE 3

Corn Particle Size Distribution Of Tailstock Generated By A
Modified Satake Maize Degermer.

| Wires/In. | % Retained Of Total Whole Corn | % Total Retained Of Tailstock |
|---|---|---|
| Sifted Tails | % | 24.87% |
| 3.5 | 28.80% | 7.16% |
| 4 | 15.72% | 3.91% |
| 5 | 38.54% | 9.58% |
| 6 | 12.17% | 3.03% |
| 8 | 3.04% | 0.76% |
| 10 | 1.01% | 0.25% |
| pan (−10) | 0.71% | 0.18% |
| Total | 100.00% | 24.87% |

TABLE 4

Corn Particle Size Distribution Of Throughstock Generated By
Modified Satake Maize Degermer.

| Wires/In. | % Retained Of Total Whole Corn | % Total Retained Of Tailstock |
|---|---|---|
| Sifted Throughs | % | 53.90% |
| 3.5 | 1.28% | 0.69% |
| 4 | 4.84% | 2.61% |
| 5 | 28.31% | 15.26% |
| 6 | 29.02% | 15.64% |
| 8 | 17.78% | 9.58% |
| 10 | 9.25% | 4.98% |
| pan (−10) | 9.53% | 5.14% |
| Total | 100.00% | 53.90% |

Understandably, the kernel fracture assembly (34) can be any of a numerous and varied conventional constructional forms used to fracture tempered whole corn (30) or whole corn (2) for the conventional dry mill process (13), or as above described using a Satake Maize Degermer or similar device, or using a modified Satake Maize Degermer as above-described, or otherwise to produce a plurality of corn particles (35) having a particle size distribution which can be separated into enriched process streams of the plurality of corn bran particles (36), the plurality of corn germ particles (37) and the plurality of corn endosperm particles (38).

The enriched process streams can be generated by numerous and varied combinations and permutations of dry mill process steps including separation of the tailstock and throughstock of a Satake Maize Degermer produced as above described, followed by combinations of sieving, aspiration, and gravity separation steps such as described by U.S. Pat. Nos. 4,181,748; 6,939,294; 7,104,479, and 7,152,818, and as described by U.S. patent application Ser. Nos. 11/268,146 and 11/726,255, each United States patent and each United States patent application incorporated by reference herein for the purpose of providing illustrative non-limiting examples of how to generate process streams enriched in particles of corn bran (19), particles of corn germ (21) and particles of corn endosperm (20) which can be utilized in the inventive wet-dry corn fractionation system (23).

Again referring primarily to FIG. 4, one non-limiting embodiment of the inventive dry-wet corn fractionation system (26) passes the plurality of corn particles (35) generated by the kernel fracture assembly (34) through a first aspirator (45) (or a plurality of first aspirators in parallel) and a second aspirator (46) (or a corresponding plurality of second aspirators in parallel), without any other process step between the first aspirator (45) and the second aspirator (46), to separate an aspirated stream (47) of the plurality of corn bran particles (35) from a non-aspirated stream (48) comprising a mixture of the plurality of corn endosperm particles (35) and the plurality of corn germ particles (34). As to certain embodiments of the invention the non-aspirated stream (47) from the first aspirator (45) enters the second aspirator (46), while in other embodiments, the aspirated stream (47) from the first aspirator (45) enters the second aspirator (46). The embodiment shown in FIG. 4 and described below is an example of the later embodiment.

The aspirated stream (47) of the plurality of corn bran particles (35) from the first aspirator (45) can contain certain of the plurality of particles of corn endosperm (35) attached to a part of the plurality bran particles (33) or attached to the plurality of corn germ particles (37) and certain particles of corn endosperm (35) and certain particles of corn germ (34) of sufficiently low mass to be aspirated by the first aspirator (31).

The a non-limiting embodiment of the double aspiration step shown in FIG. 4, also provides an example of processing the "tails" and the "throughs" from kernel fracture assembly (34) of a modified Satake Degermer as above-described. Each of the throughs and tails separately pass separately through a first aspirator (45A) (45B) to generate a mixture of the plurality of corn endosperm particles (38) and the plurality of corn germ particles (37) and a first aspirated plurality of corn particles (49). The first aspirated plurality of corn particles (49) passes through the second aspirator (46) to generate a mixture of the plurality of corn endosperm particles (38) and the plurality of corn germ particles (37) and a second aspirated plurality of corn particles (50) which largely contains the plurality of corn bran particles (36) but also contains some amount of the plurality of corn germ particles (37) and some amount of the plurality of corn endosperm particles (38). A non-limiting example of the first aspirator(s) (45) and the second aspirator(s) (46) can be a Kice, Series E six path unit available from Kice Industries, Inc., 5500 North Mill Heights Drive, Wichita, Kans. The determination of the correct air setting for the first aspirator (45A) through which the "tails" pass and the first aspirator (45B) through which the "throughs" pass can be made by achieving a particle profile which includes mixture of the plurality of corn endosperm particles (38) and plurality of corn germ particles (37) comprising about 95% of the non-aspirated stream (48) by weight of each of the first aspirators (45A) (45B). An advantage of utilizing a first aspiration step and a second aspiration step over conventional process methods can be removal of the plurality of corn bran particles (36) and part of the plurality of corn endosperm particles (38) and part of the plurality of corn germ particles (37) of sufficiently low mass to be aspirated in the first aspirated plurality of corn particles (49) and second aspirated plurality of corn particles (50) which contain the vast majority of the water content in the plurality of particles (35) delivered from the corn fracture assembly (34) which allows for more ready sifting of the non-aspirated stream (48) of the plurality of corn endosperm particles (38) and the plurality of corn germ particles (37).

Figure 1:
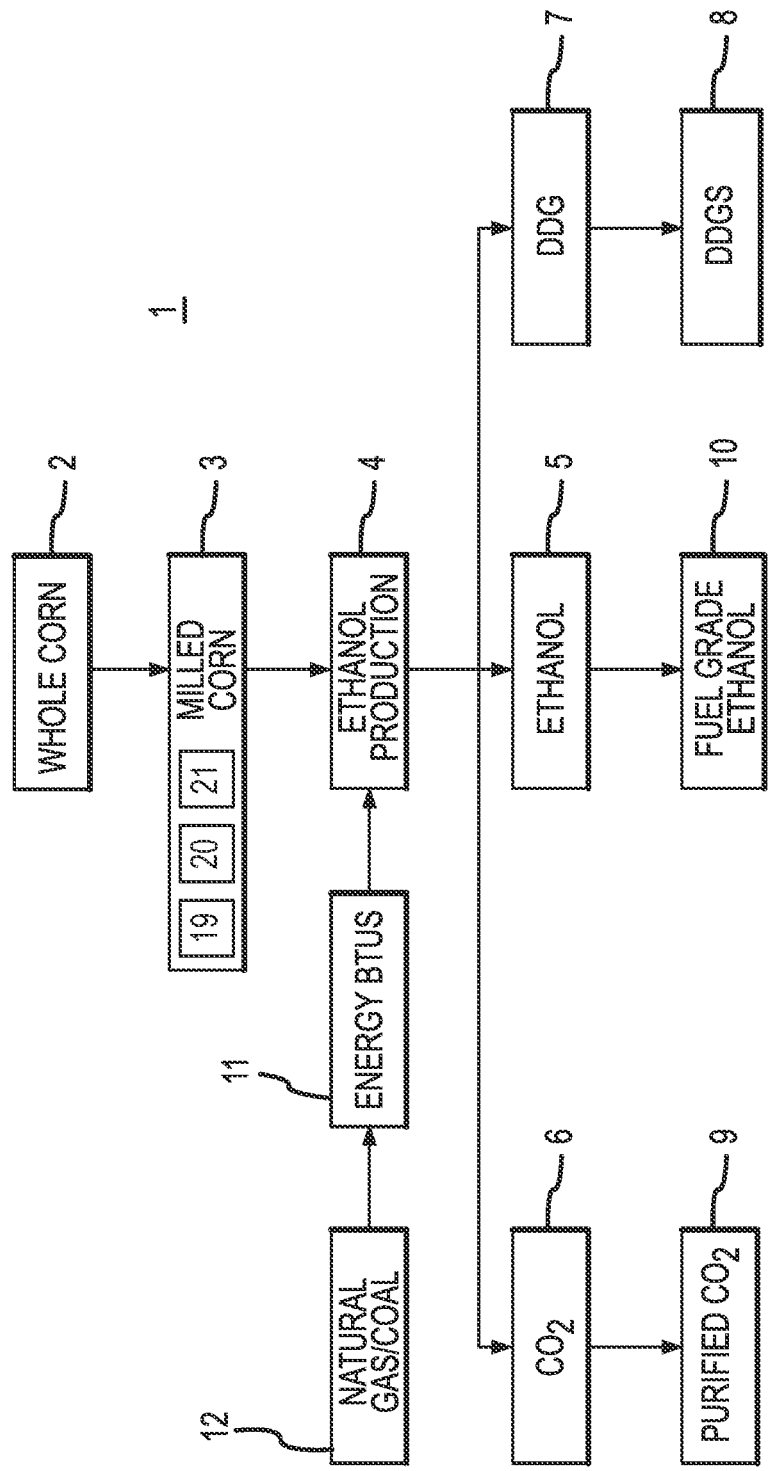
FIG. 1 is a block flow diagram of a particular conventional corn mill process which generates milled corn coupled to an ethanol production process.
Figure 2:
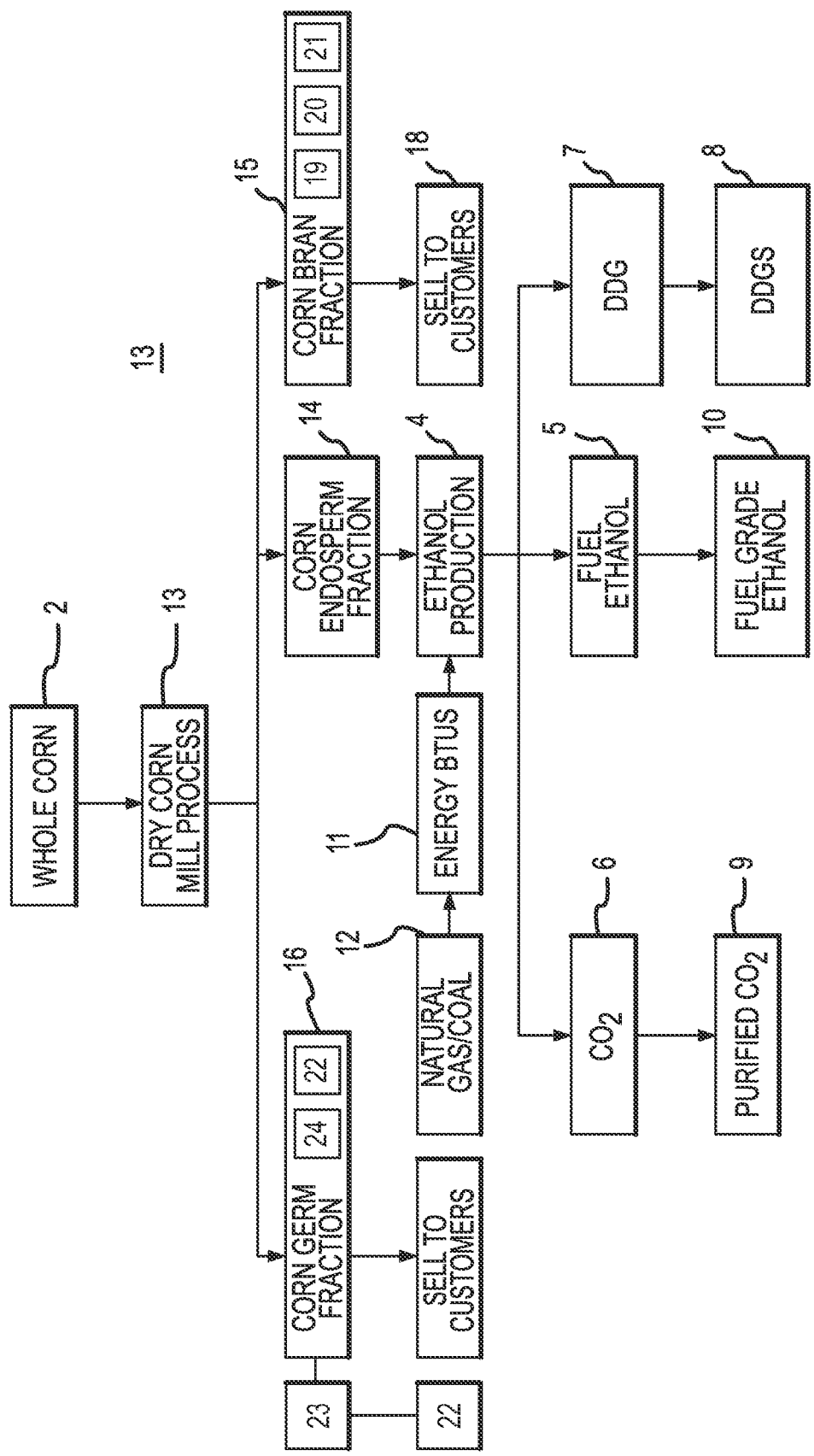
FIG. 2 is a block flow diagram of a particular dry corn mill process which generates corn fractions coupled to an ethanol production process.
Figure 3:
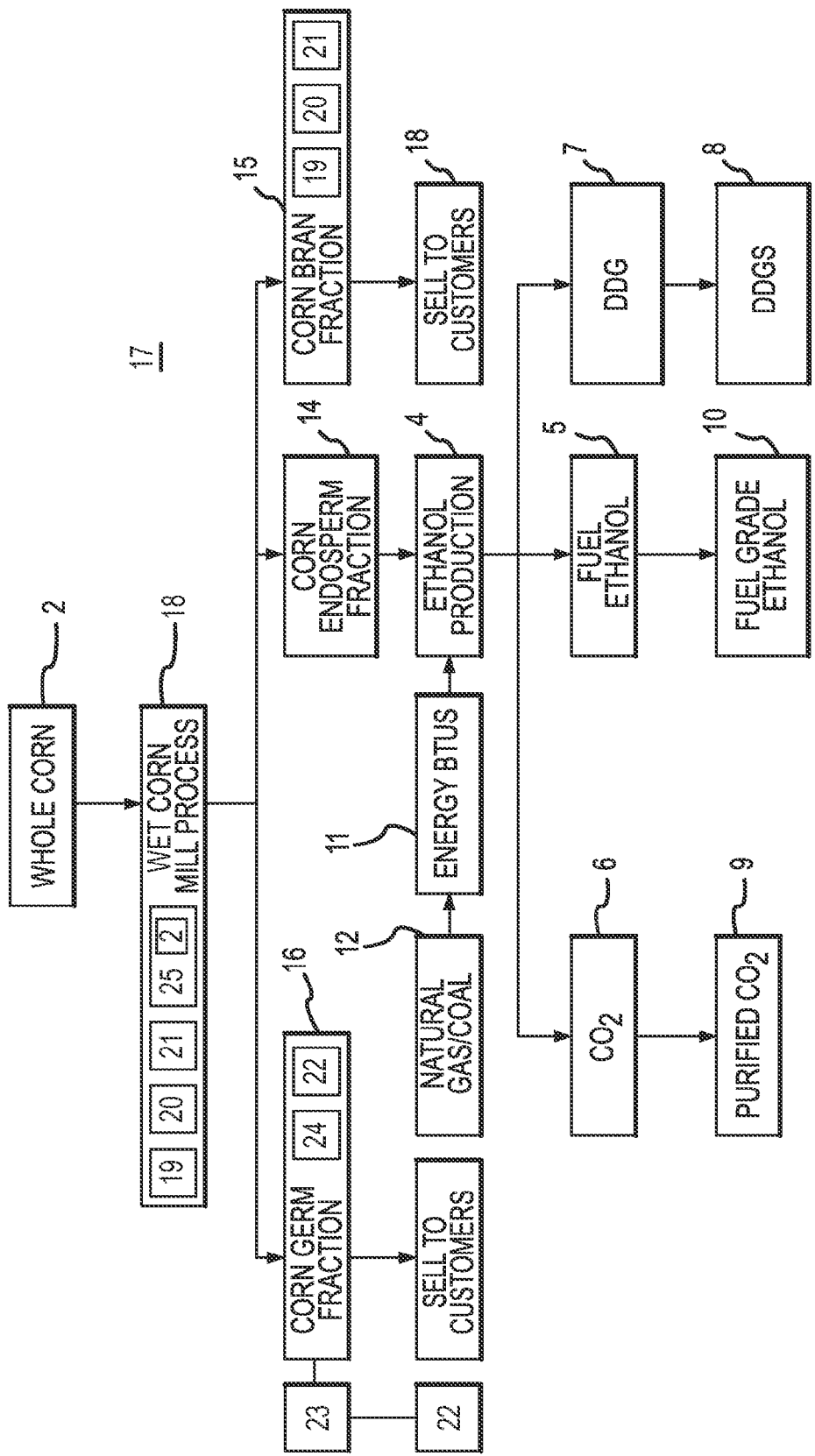
FIG. 3 is a block flow diagram of a particular wet mill process which generates corn fractions coupled to an ethanol production process.

Again referring primarily to FIG. 3, the non-aspirated stream (48) of the plurality of corn endosperm particles (38) and the plurality of corn germ particles (37) from the first aspirator(s) (45) (45A) (45B) can be accepted by a first sifter (51) which generates a first plurality of streams of sifted particles (52) by retaining a part of the plurality of corn endosperm particles (29) and a part of the plurality of corn germ particles (37) on a plurality of screens between the range of about 3.5 wires per inch to about 16 wires per inch. A certain non-limiting embodiment of the first sifter (51) can have a 3.5 wire screen, a 5 wire screen, a 6 wire screen, a 10 wire screen, a 12 wire screen, and a 16 wire screen although other combinations of screens in the range could also be utilized. Similarly, the non-aspirated mixture (48) of the plurality of corn endosperm particles (38) and corn germ particles (37) from the second aspirator (46) can be accepted by a second sifter (53) to generate a second plurality of sifted streams (54) of the plurality of endosperm particles (38) and the plurality corn germ particles (37) by retaining a part of the plurality of corn endosperm particles (38) and a part of the plurality of corn germ particles (37) on a plurality of screens between the range of about 10 wires per inch to about 40 wires per inch. A certain non-limiting embodiment of the second sifter (53) can have a 10 wire screen, a 12 wire screen, a 16 wire screen, a 20 wire screen, a 24 wire screen, a 32 wire, and a 40 wire screen although other combinations of screens in the range can be utilized. The second sifter (53) in the embodiment shown can also accepts the −16 particles (particles falling through a 16 wire screen) from the first sifter (51) (although these corn particles not retained by the first sifter (36) will be the pass through of the smallest selected screen). As a non-limiting example, a Great Western "HS" Sifter available from Great Western Manufacturing, 2017 South 4$^{th}$ Street, Leavenworth, Kans. 66048-0149 can be suitable for use as above-described.

Of the plurality of streams of sifted particles (52) (54) generated by the first sifter (51) and the second sifter (53) of greater than about 16 wire can be accepted by a corresponding plurality of first gravity separators (55). In the non-limiting example provided above each of the plurality of streams of sifted particles (52) (54) retained by the 5 wire screen, the 6 wire screen, the 8 wire screen, the 10 wire screen and the 16 wire screen can be accepted by a corresponding one of the plurality of first gravity separators (55). Each of the plurality of first gravity separators (55) can generate three separator streams including a plurality of corn endosperm particles (38); a mixture of corn endosperm particles and corn germ particles (56), and a plurality of corn germ particles (37). The separator streams which include the plurality of corn endosperm particles (38) from each first separator (55) can be accepted into the corn endosperm fraction (14) which can be directed to a corn endosperm storage unit (57). The separator streams including the mixture of corn endosperm particles and the plurality of corn germ particles (56), and the plurality of corn germ particles (37) can each be accepted by a corresponding one of a plurality of second gravity separators (58) each of which generates two second separator streams including the plurality of corn endosperm particles (38) and the plurality of corn germ particles (37). The plurality of corn endosperm particles (38) can be accepted by the corn endosperm fraction storage unit (44) and the plurality of corn germ particles (37) accepted in the corn germ fraction (16) and delivered to a corn germ fraction storage unit (59). A non-limiting example of a gravity separator can be a Forsberg Vacuum Gravity Separator, Model 50-VMS available from Forsberg, Inc., P.O. Box 510, 1210 Pennington Avenue, Thief Rivers Falls, Minn. 56701. A plurality of corn germ particles (37) can be retained by the second sifter (53) on screens having range of about 20 wire to about 40 wire which can be accepted by a third aspirator (60).

The second aspirated plurality of corn particles (50) from the second aspirator (46) can be accepted by a corn bran finisher (61). The corn bran finisher (61) operates to remove an amount of bound corn endosperm (62) from the plurality of corn bran particles (36) to generate a mixture of the plurality of corn endosperm particles (38) and the plurality of corn germ particles (37) and a stream of corn bran particles (27). As a non-limiting example, a Kice Bran Finisher, Model BF42 can be utilized to accept the second aspirated plurality of corn particles (50).

The stream of the plurality of corn bran particles (36) can be accepted into the bran fraction (15) and delivered to a corn bran fraction storage unit (63). The plurality of corn germ particles (37) and plurality of corn endosperm particles (38) from the corn bran finisher (61) can be accepted by a third sifter (64) having a range of screens between about 20 wires per inch and 40 wires per inch. A non-limiting example of a third sifter (64) can provide a 20 wire screen, a 24 wire screen, a 32, wire screen, and a 40 wire screen. A suitable third sifter (64) can be a Great Western "HS" Sifter. The plurality of corn germ particles (37) retained by the third sifter (64) in the range of between about the 20 wire screen and the 40 wire screen can be accepted by the third aspirator (60) along with the plurality of corn germ particles (37) retained by the second sifter (53) in the range of between about the 20 wire screen and the 40 wire screen. The plurality of corn endosperm particles (38) passing through the 40 wire screen of the second sifter (53) and the third sifter (60) can be accepted into the corn endosperm fraction (14) by the corn endosperm fraction storage unit (57).

The non-aspirated stream (48) from the third aspirator (60) comprised largely of a plurality of corn germ particles (37) can be accepted by a plurality of roller mills (65) which operate to increase the size of the plurality of corn germ particles (37) and reduce the size of the plurality of corn endosperm particles (38). A suitable non-limiting example of a roller mill (65) can be a Model 100/30-4A Pick-Up available from GBS Group S.p.a, Corso Stati, 7-Padova-Italy. The plurality of corn germ particles (37) and the plurality of corn endosperm particles (38) from each roller mill (65) can be accepted by a fourth sifter (66) having a plurality of screens in the range of between about 20 wires per inch and about 40 wires per inch. The plurality of corn germ particles (37) retained by the plurality of screens between about 20 wires per inch and about 40 wires per inch can be accepted into the corn germ fraction (16) and delivered to corn germ fraction storage unit (595). The plurality of corn endosperm particles (38) which pass through the screen having about 40 wires per inch can be accepted by the corn endosperm fraction (14) or delivered to the corn endosperm storage unit (57).

The inventive dry corn fractionation system (17) can produce end material balances by weight percent for each corn fraction (14) (15) (16), as follows:
Germ %: about 8.0 to about 9.0
Bran %: about 6.0 to about 6.4
Endosperm %: about 85.0 to about 86.0

In addition to the end material balances by weight percent for each corn fraction (14) (15) (16), which can be produced by the dry corn mill process (13) above described, certain embodiments can produce each corn fraction (14) (15) (16) with advantageous ratios of fat, fiber, and starch by weight percent, as follow:

|  | Fat % | Fiber % | Starch % |
| --- | --- | --- | --- |
| Germ Fraction (45) | 20% min. | 25% max. | 35.0% max. |
| Bran Fraction (49) | 6% max. | 75% min. | 15.0% max. |
| Endosperm Fraction (44) | 1.5% max. | 2.0% max. | 82.5% min. |

Additionally, certain embodiments of the dry corn mill process (13) above described can achieve these advantageous ratios and material balances concurrently which allows a high purity endosperm fraction (14) of at least about 82% with starch loss (compared to clean whole corn (2)) of not greater than about 4%.

However, the material balances and ratios for the corn fractions (14) (15) (16) generated by the dry corn mill process (13) whether produced in accordance with the example of a dry corn mill process (13) above-described or produced as described in any of the United States patents and patent applications above indicated, or by another dry corn mill process (13) may not sufficiently increase the percent corn oil (22) content (also referred to as Fat %) or sufficiently decrease the amount of endosperm (20) or starch content (also referred to as Starch %) of the corn germ fraction (16) on a dmb, or may not sufficiently increase the purity of the endosperm fraction (14) or starch content (Starch %) or sufficiently decrease the amount of corn germ (21) or content of corn oil (22) (Fat %) of the corn endosperm fraction (14), or may not decrease the amount of corn endosperm (20) or starch content (Starch %) of the corn bran fraction (15). The material balances and ratios can be altered or adjusted by use of the inventive dry-wet corn fractionation system (26) further described below.

Figure 5:
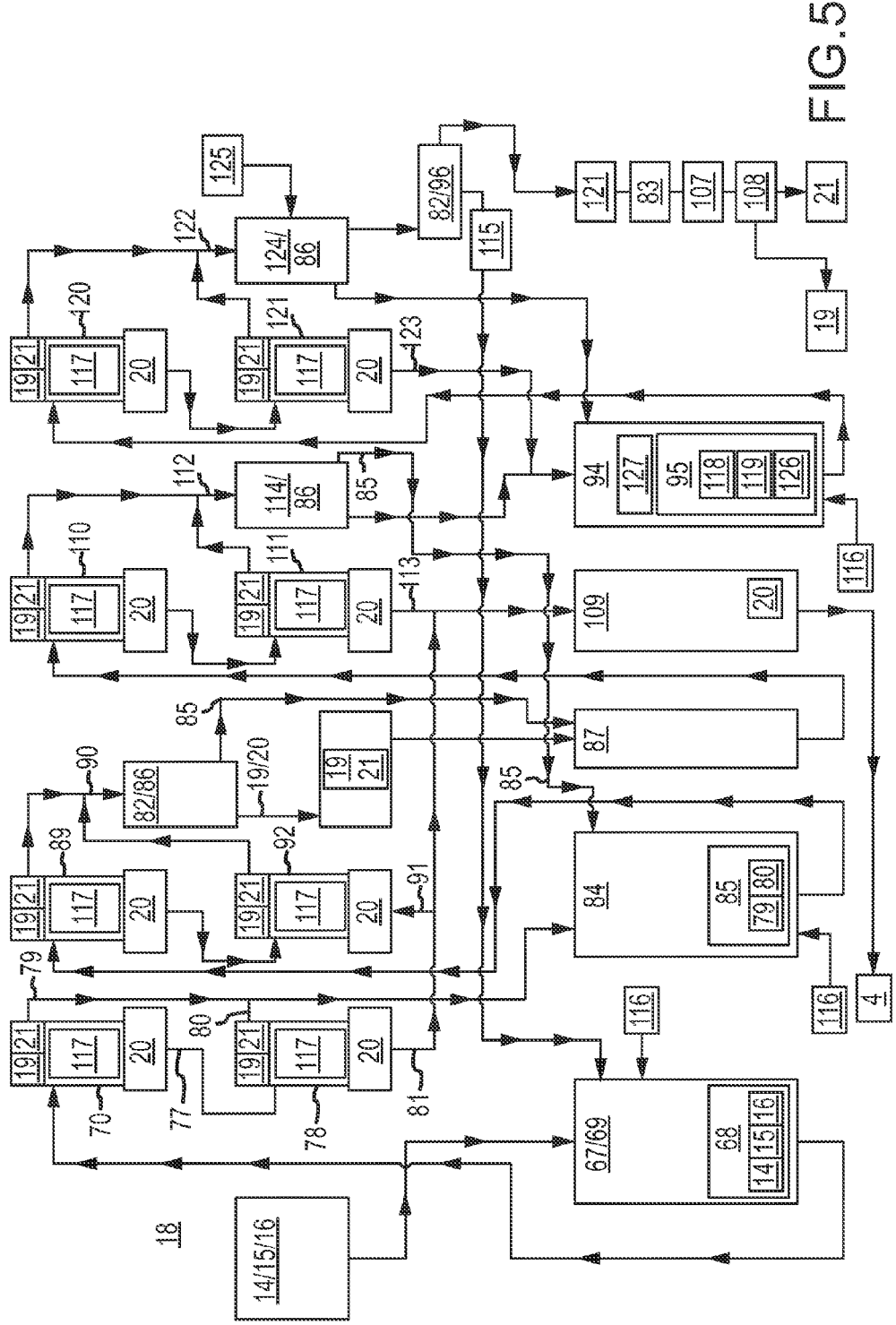
FIG. 5 is a block flow diagram of a particular embodiment of wet mill process of the inventive dry-wet corn mill fractionation system.

Now referring primarily to FIG. 5, as to certain embodiments of the inventive dry-wet corn fractionation system (26) the resulting germ fraction (16) (or the resulting endosperm fraction (14), or the resulting bran fraction (15), or other grain fraction) can be further processed in accordance with the following wet process whether in whole or in part. While the description provided below provides examples in the context of further processing the germ fraction (16), the invention is not so limited and the wet process portion of the dry-wet fractionation system (26) can be utilized to further process a corn bran fraction (15) or a corn endosperm fraction (14), including dry corn mill process (13) streams conventionally referred to as "high fat meal" and other similar dry corn mill process (13) streams. Additionally, while the wet process described herein can be applied to a dry corn mill process (13) fraction (14) (15) (16), it is not intended to preclude application of the inventive dry-wet corn fractionation system (26) or portions or steps thereof to dry mill process grain fractions of other grains, such as wheat, rice, rye, soy bean, or the like, which have similar, endosperm, germ and bran fractions.

Again referring primarily to FIG. 5, a dry corn mill process (13) fraction (14) (15) (16) (or other grain fraction) can be transferred to a mix tank (67) and combined with a mix liquid (68) in a ratio in a range of about 1.5:1 and about 2.5:1 (mix liquid (68):dry corn mill process fraction (14) (15) (16) weight to weight ("wt./wt.")). Particular embodiments utilize a ratio of about 2:1 mix liquid (68): germ fraction (16) wt./wt., or about 2:1 mix liquid (68): endosperm fraction (14) wt./wt., or about 2:1 mix liquid (68):bran fraction (15). In the context of the germ fraction (16), as a non-limiting example also applicable to other dry mill process (13) grain fractions (14) (15), the germ fraction (16) can be combined with the mix liquid (68) in the mix tank (67). The germ fraction (16) can be mixed for a period of time in the range of about 15 seconds and about 300 seconds. However, the period of time, depending grain fraction, can be selected from the group consisting of: about 15 seconds to about 60 seconds, about 45 seconds and about 75 seconds, about 60 seconds to about 90 seconds, about 75 seconds to about 105 seconds, about 90 seconds and about 120 seconds, about 105 seconds and about 135 seconds, about 120 seconds and about 180 seconds, about 150 seconds to about 210 seconds, about 180 seconds and about 240 seconds, 210 seconds and about 270 seconds, and about 240 seconds to about 300 seconds. The period of time can be sufficient in length to allow the grain fraction (14) (15) (16) to be processed by a rotational flow of the grain fraction in the mix liquid (68), as described below.

Additionally, the above described ratios of the mix liquid (68) to the germ fraction (16) (or other grain fraction) and the above described range of duration of time for mixing of the germ fraction (16) (or other fraction) with the mix liquid (68) is not intended to be limiting and certain embodiments of the inventive dry-wet grain fractionation system (26) can utilize lesser or greater ratios of mix liquid (68) to the germ fraction (16) (or other grain fraction) or a greater or lesser period of time for mixing the germ fraction (16) (or other fraction) with the mix liquid (68). The ratio of mix liquid (68) to the germ fraction (16) can also be expressed in terms of the amount of mix liquid (68) to an amount of germ (21) within the germ fraction (16) on a dry mass basis wt./wt. In those instances, the ratio of the mix liquid (68) to amount of germ (21), will be higher, for example 11.0-12.0 parts mix liquid (68) to 1 part germ (21).

The term "mix liquid (68)" can mean any liquid in which the germ fraction (16) or other dry mill process (13) grain fraction can be compatibly combined to perform the subsequent process or steps below described; however, the mix liquid (68) will typically be one or more of a liquid of a downstream process step, the centrate (115) from a decantor (96), water, well water, municipally treated water, filtered water, or the like, and which can have a chemistry variable to a degree based upon the source and to the extent reacted with atmospheric carbon dioxide or scrubbed of carbon dioxide (individually or collectively or in various combinations "water" (116)). The mix liquid (68) can be adjusted by the addition of acid (such as hydrochloric acid) or base (such as sodium hydroxide) to a particular pH in a range of about 6 pH and about 8 pH and may further include an amount of oil or an amount of starch as may be released from the corn germ fraction (16) or the corn endosperm fraction (14) to the mix liquid (68) or in the centrate (115).

Embodiments of the inventive dry-wet corn fractionation system (26) can utilize a mix tank (67) having a capacity sufficient to mix the amount of germ fraction (16) (or other process fraction) and mix liquid (68). The mix tank (67) can further provide a mixer element (69) such as a mechanical paddle, aerator, screw, or the like to mix the corn germ fraction (16) with the mix liquid (68). Mixing the combination of the corn germ fraction (16) in the mix liquid (68) can, as a separate step or in combination with the steps described below, allow particles of corn endosperm (20) bound or otherwise associated with the corn germ (21) to transfer to the mix liquid (68) to allow subsequent separation of the endosperm (20) or starch from the corn germ fraction (16) (or other grain fraction).

Now referring primarily to FIGS. 5 and 6, the mixed combination of the corn germ fraction (16) (or the endosperm fraction (14), bran fraction (15) or other grain fraction) and the mix liquid (68) can be transferred from the mix tank (68) to a first centrifugal force separator (70) which converts the linear motion of the transferred mixture of the germ fraction (16) (or other grain fraction) and mix liquid (68) to a rotational motion or rotational flow within the first centrifugal force separator (70). This conversion can be accomplished by introducing the mix liquid containing the germ fraction (16) through a feed inlet (71) tangentially into the upper cylindrical portion (72) of a cylindrical-conical chamber (73) at sufficient velocity to form a rotational flow (117) having sufficient flow characteristics to distribute the lighter materials toward the first outlet (74) and the heavier materials toward the second outlet (75) of the first centrifugal force separator (70) (similarly as to each additional centrifugal force separator). The rotational flow (117) of the mix liquid (68) within the first centrifugal force separator (70) (or any of the centrifugal force separators) allows a portion of the mix liquid (68) containing the relatively lighter particles of corn germ (21) (and other lighter particles such as corn bran (19)) to discharge through the first outlet (74) of the first centrifugal force separator (70) located proximate or at the center-top of the cylindrical portion (72) of the cylindrical-conical chamber (73) (also referred to as the "first centrifugal force separator over flow" (70) or as to any of the centrifugal force separators the "overflow"). The remaining mix liquid (68) in which the relatively heavier particles of endosperm (20) are suspended can be discharged through a second outlet (75) of the first centrifugal force separator (70) located proximate or at the apex of the conical portion (76) of the cylindrical-conical chamber (73) (also referred to as the "first centrifugal force separator under flow" (77) or as to any of the centrifugal force separators the "under flow"). The cylindrical-conical chamber (73) may have no moving parts and separation of the lighter particles of corn germ (21) in the first centrifugal force separator over flow (79) from the heavier particles of endosperm (20) in the first centrifugal force separator under flow (77) can depend solely upon the internal surface configuration of the cylindrical-conical chamber (73) and the rotational flow characteristics of the mixture of the germ fraction (16) (or the endosperm fraction (14) (or other fraction) and the mix liquid (68) within the cylindrical-conical chamber (73) such as inlet pressure, volume, velocity, viscosity, and concentration of the germ fraction (16) in the liquid, the shape and the size of the suspended germ particles (21) and endosperm particles (20), the specific gravities of the particles of the corn germ fraction (16) or the particles of the corn endosperm fraction (14), or the particles of the corn bran fraction (15), or the like. The first centrifugal force separator (70) (and other centrifugal force separators) can be located in a vertical or horizontal or other orientation (see FIG. 7) and although the embodiments of the invention shown in FIG. 5 show each of centrifugal force separators in substantially vertical orientation, the invention is not so limited.

Various constructional forms of the first centrifugal force separator (70) can be produced or purchased which are suitable for use in the above-described separation of the germ particles from the endosperm particles of the mixture of the germ fraction in water. As non-limiting examples, the first centrifugal force separator (70) (or other centrifugal force separators) can take the form of a Hydrocyclone which can be purchased from FLSmidth-Krebs, POB, Landenberg, Pa., USA. In general, Hydrocyclones can have an inlet (71) diameter in the range of about one-half inch to about 8 inches. A hydrocyclone having a one inch inlet can process a stream of water having a pressure in the range of about 4 pounds per square inch ("psi") to about 6 psi at a rate in a range of about 8 gallon per minute ("gpm") to about 15 gpm. A hydrocyclone having a two inch inlet can process a stream of water having a pressure in the range of about 4 psi to about 6 psi at a rate in a range of about 48 GPM to about 75 GPM. Particular embodiment of the inventive wet-dry corn fractionation system (23) can utilize a first centrifugal force separator (70) (and subsequently described centrifugal force separators) in the form of Hydrocyclone having an inlet diameter in the range of about one inches and about four inches.

A mixture of the corn germ fraction (16) and mix liquid (68) (about 1:2 wt./wt.) can be transferred from the mix tank (67) to the first Hydrocyclone (70) at a pressure in the range of about 20 psi and about 40 psi at a rate in the range of about 15 gpm and about 600 gpm depending on the diameter. With respect to proper configuration of the first centrifugal force separator (70) or any additional centrifugal force separator described below, see also, Arterburn, Richard, A, *The Sizing and Selection of Hydrocyclones*, FLSmidth-Krebs, POB, Landenberg, Pa., USA (2008), hereby incorporated by reference herein.

Figure 7:
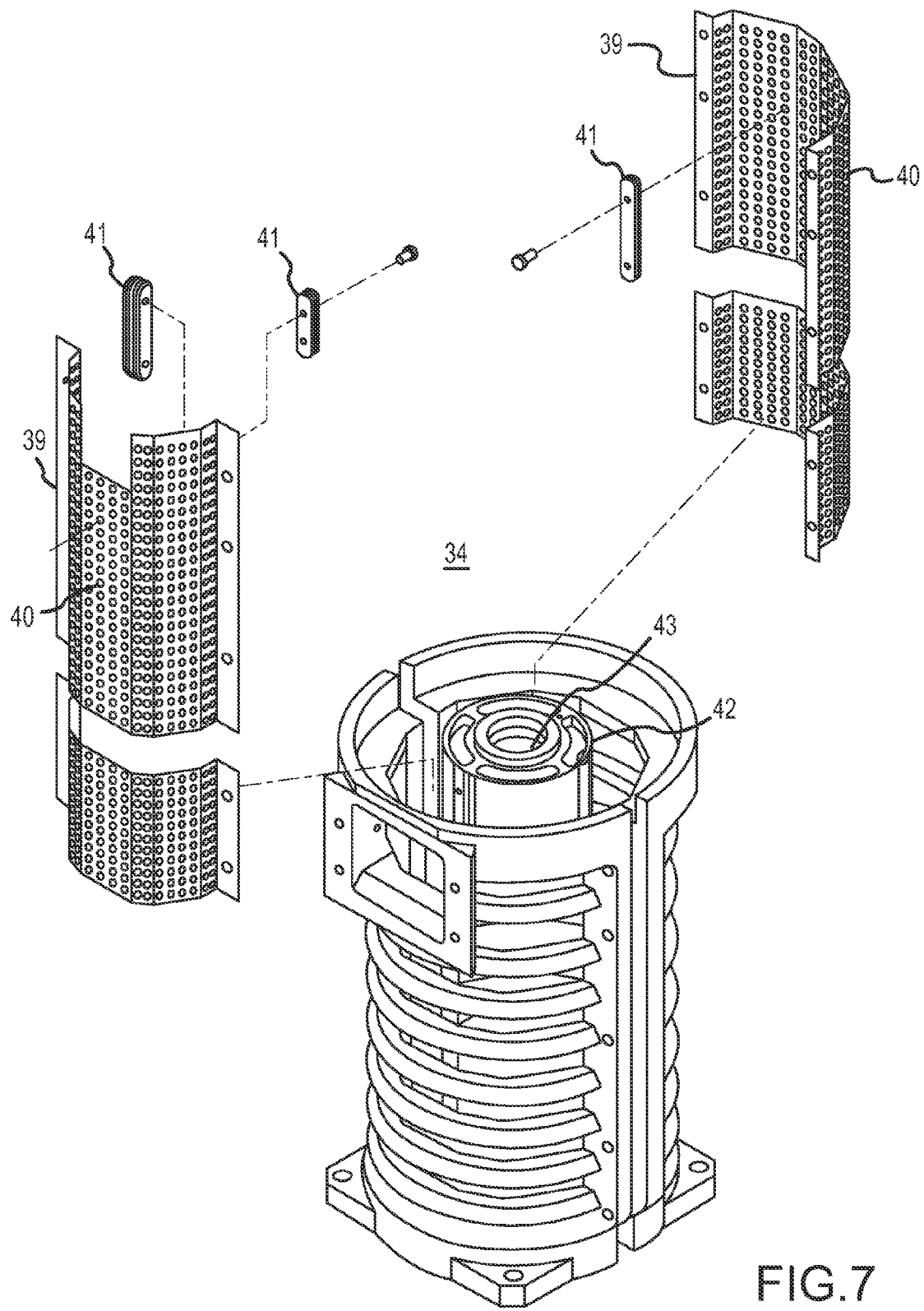
FIG. 7 is an exploded diagram of part of a modified Satake Maize Degermer which can be utilized in the inventive dry-wet corn fractionation system.

Now referring primarily to FIGS. 5 and 7 and Table 5, the first centrifugal force separator under flow (77) can consist substantially of particles of corn endosperm (20) suitable for introduction into an ethanol production system (4). Other embodiments of the invention can further include a second centrifugal force separator (78). A Hydrocyclone as above described can be utilized as the second centrifugal force separator (78); although the invention is not so limited. The first centrifugal separator under flow (77) can be transferred to the second centrifugal force separator (78) through the feed inlet (71) at a pressure in the range of about 20 psi and about 40 psi at a rate in the range of about 15 gpm and about 600 gpm. The second centrifugal force separator (78) operates in the same or similar fashion as above described for the first centrifugal force separator (71) to generate a second centrifugal force separator overflow (80) which contains the relatively lighter particles of corn germ (21) (and particles of corn bran (19)) and a second centrifugal force separator underflow (81) which contains the relatively heavier particles of corn endosperm (20). The second centrifugal force separator under flow (81) from the second centrifugal force separator (78) consisting substantially of particles of corn endosperm (or other grain endosperm) can be transferred to the ethanol production system (4).

Again referring primarily to FIGS. 5 and 7 and Table 5, the first centrifugal force separator overflow (79) and the second centrifugal force separator overflow (80) consisting substantially of corn germ (12) and corn bran (19) can be directed separately or in combination to liquid removal device (82)

such as a gravity screen (86), a germ press, decanter (96) centrifuge, paddle screen, or the like. The resulting moist corn germ (21) and corn bran (19) can then be transferred to a dryer (83) to lower moisture in the corn germ (21). The dryer (83) can be any of a numerous and varied constructional form such as a rotary steam tube or fluid bed drier. The moisture content of the corn germ (21) after drying can be less than about 10% wt./wt., or can be less than about 5% wt./wt., or less than about 4% wt./wt. The resulting corn germ fraction (16) can have a starch content of less than about 14% wt./wt., less than about 12% wt./wt., less than about 11% wt./wt. and less than about 10% wt./wt., or less than about 6% wt./wt. As to certain embodiments the germ product can have starch content in the range of about 6% wt./wt. and about 8% wt./wt., or even less than 6% wt./wt. The reduction of starch content and reduction in other leachable materials from the corn germ (21) contained in the first centrifugal force separator overflow (79) and the second centrifugal force separator overflow (80) whether separately or in combination can correspondingly increase the oil content of the corn germ (21). The oil content of the germ (21) on a dry matter basis can be increased to about 30%, or about 35%, or about 40%, or about 50%, or about 55%. The PDI can be about 45% or greater.

While the germ product of conventional wet milling may have similar oil content, the PDI content can be about 26% or lower. See for example, U.S. patent application Ser. No. 117, 621, Publication No. 20080279983, hereby incorporated by reference.

Again referring primarily to FIG. 5 and FIG. 7 and Table 5, the first centrifugal force separator overflow (79) and the second centrifugal force separator overflow (80) separately or in combination can be alternately directed to a first soak tank (84). Additional, first soak liquid (85) which can be water as above described or liquid separated from the germ (21) or the bran (21) in a downstream process step (as shown for example in FIG. 5) can be added to the amount of the first centrifugal force separator overflow (79) and the second centrifugal force separator overflow (80) to provide an amount of first soak liquid (85) in which the germ (21) and the bran (21) in the overflow can be soaked for a period of time to suspend, loosen or remove adhered or associated corn endosperm (20), or allow proteins and other leachable moieties in the corn germ (21) to transfer to the first soak liquid (85). In a particular embodiment of the dry-wet corn fractionation system (26), the particles of corn germ (21) in the overflow (79) (80) from the first centrifugal force separator (70) and the second centrifugal force separator (78) can be soaked for a duration of time in the range of about thirty minutes to about 120 minutes, or in a range of about 60 minutes to about 120 minutes, or in a range of about 90 minutes to about 120 minutes. The temperature of the first soak liquid (85) can be in a range of at least ambient temperature and about 82° C. (about 180° F.), or as to other embodiments in a range of about 12° C. (about 55° F.) to about 82° C. (about 180° F.), or as to other embodiments in a range of about 48° C. (about 120° F.) to about 82° C. (about 180° F.), and in another embodiment can be about 60° C. (about 140° F.) to about 70° C. (about 160° F.).

Again referring to FIG. 5, the soaked particles of corn germ (21) and corn bran (19) and the first soak liquid (85) from the first soak tank (84) can be transferred to a first liquid removal device (82), such as a gravity screen (86), which operates to separate the first soak liquid (85) from the soaked particles of germ (21) and bran (19). The separated first soak liquid (85) can be directed from the gravity screen (86) to a collection tank (87). The separated soaked particles of germ (21) can be directed to a comminutor or grinder (88) to reduce the size of the soaked particles of germ (21) and bran (19) and to loosen attached endosperm (20). A grinder (88) suitable for use with the dry-wet corn fractionation process (26) can be a Bauer mill such as Model 148-2; however, the invention is not so limited. Another grinder (88) suitable for use with the inventive suitable for use with the dry-wet corn fractionation process (26) can be a disc mill such as a single or double disc mill such as Model DM 24 or DH 24 available from Andritz AG, Stattegger Strasse 18, A-8045 Graz, Austria. The ground soaked particles of germ (21) can then be transferred to the collection tank (87) and re-mixed with the first soak liquid (85).

As to particular embodiments of the invention, prior to the step of separation of the soaked particles of corn germ (21) and corn bran (19) from the first soak liquid (85) of the first soak tank (84), the first soak liquid (85) containing particles of germ (21) and bran (19) can be transferred to a third centrifugal force separator (89) with the overflow containing particles of corn germ (21) and corn bran (19) directed to the inlet (71) of a fourth centrifugal force separator (92) each of which operates in the similar manner to the first centrifugal force separator (70) and the second centrifugal force separator (78), as above-described. Operation of the third and fourth centrifugal force separators (89) (92) separates the relatively lighter particles of germ (21) (and other lighter particles such as bran particles (19)) to discharge through a first outlet (74) of the third and fourth centrifugal force separators (89) (92) (also referred to as the "third and fourth centrifugal force separator over flow") (90). The remaining first soak liquid (85) in which the relatively heavier particles of endosperm (20) are suspended can be discharged through a second outlet (75) of the third and fourth centrifugal force separators (89) (92) located proximate or at the respective apexes of the conical portion (76) of the cylindrical-conical chamber (73) (also referred to as the "third and fourth centrifugal force separator under flow") (91). The overflow (90) directed to the liquid separator (82) in the form of a gravity screen (86), as above described. The underflow (91) can be directed to an underflow collection tank (109) or directly to an ethanol production system (4).

Again referring primarily to FIGS. 5 and 7, as to particular embodiments of the invention, the combination of the ground soaked particles of germ (21) and bran (19) and first soak liquid (85) can be transferred from the collection tank (87) to a fifth centrifugal force separator (110) with the overflow containing particles of corn germ (21) and corn bran (19) directed to the inlet (71) of a sixth centrifugal force separator (111) each of which operates in the similar manner to the first centrifugal force separator (70) and the second centrifugal force separator (78), as above-described. Operation of the fifth and sixth centrifugal force separators (110) (111) separates the relatively lighter particles of germ (21) (and other lighter particles such as bran particles (19)) to discharge through a first outlet (74) of the fifth and sixth centrifugal force separators (110) (111) (also referred to as the "fifth and sixth centrifugal force separator over flow") (112). The remaining first soak liquid (85) in which the relatively heavier particles of endosperm (20) are suspended can be discharged through a second outlet (75) of the fifth and sixth centrifugal force separators (110) (111) located proximate or at the respective apexes of the conical portion (76) of the cylindrical-conical chamber (73) (also referred to as the "fifth and sixth centrifugal force separator under flow") (113). The overflow (112) can be directed to a second liquid separator (114), such as a gravity screen (86), as above described. The separated liquid comprising the remaining portion of the first soak liquid (85) can be returned to the first soak tank (84) and supplemented with water (116), if necessary. The underflow (113) can be directed to the endosperm collection tank (109) or directly to an ethanol production system (4).

Now referring primarily to FIG. 5, the moist germ (21) and bran (19) from the second liquid separator (114) be transferred to a second soak tank (94) and mixed in an amount of second soak liquid (95). The second soak (95) can in part comprise liquid removed from the germ (21) and the bran (19) in a downstream liquid removal step, such as from the decantor (96). The germ (21) the bran (19) can be soaked for a period of time in the range of about 360 and about 720 minutes at a temperature in a range of at least ambient temperature and about 82° C. (about 180° F.), or as to other embodiments in a range of about 12° C. (about 55° F.) to about 82° C. (about 180° F.), or as to other embodiments in a range of about 48° C. (about 120° F.) to about 82° C. (about 180° F.), and in another embodiment can be about 60° C. (about 140° F.) to about 70° C. (about 160° F.).

In yet another embodiment, an enzyme (118) such as a carbohydrase may be added to the second soak liquid (95) to aid in removal of bound starch. Examples of such enzymes include amylo-glucosidases which convert oligosaccharides to individual glucose molecules; proteases which break down protein structure; and cellulases. Other enzymes may be added in combination with alpha amylase or separately, but not limited to include: a hemi cellulase, pullulanase, glucoamylase, dextrinase, phytase, lipase or pectinases. In one embodiment, such an enzyme can be an alpha amylase enzyme. Adding an enzyme (118) can disrupt the starch linking bonds to afford a shorter soak time. In an addition, sulfur dioxide (119) may be but is not necessarily added to the second soak liquid (95). Sulfur dioxide (119) can further reduce the possibility of contamination and further aid in separating the starch from the germ (21) and bran (19). When soaked with sulfur dioxide (119), it is expected the disruption of sulfur bonds can be achieved at a lower temperature in a range of about 48° C. (about 120° F.) and about 52° C. (about 125° F.).

Now referring to FIGS. 5 and 8, the corn germ (21) and bran (19) from the second soak along with the second soak liquid (95) can be transferred to a decanter (96) which operates to separate the germ (21) from the second soak liquid (95). A decanter (96) suitable for use in the dry-wet corn fractionation system (26) is available from Flottweg AG, Industriestra Be 6-8, 84137 Vilsbiburg, Germany or Flottweg Separation Technology, Inc., 10700 Toebben Drive, Independence, Ky. 41051. The mixture of the germ (21) and bran (19) and the second soak liquid (95) can be fed through a fixed central pipe (97) into the distributor (98) located in the scroll body (99). The germ (21) can then be accelerated in circumferential direction and passes through feed ports (100) in the scroll body (99) into the separation section (101) of the bowl (102). The bowl (102) has a cylindrical-conical shape and rotates at a pre-set speed specific to the particular embodiment of the invention. The mixture of the germ (21) and bran (19) and the second soak liquid (95) rotates with the bowl (102) at the operating speed and forms a concentric layer (103) around the bowl wall (104). The germ (21) and bran (19) contained in second soak liquid (95) can be deposited against the bowl wall (104) under the influence of centrifugal force. The length of the cylindrical bowl (102) and the cone angle (105) are selected to meet the specific requirement of an embodiment of the invention. The scroll (99) rotates at a slightly different speed to that of the bowl (102) and conveys the deposited second soak germ (21) towards the conical end (105) of the bowl (102). The residence time can be adjusted by changing the differential speed of the scroll (99) to provide optimum separation for the particular mixture of second soak germ (21) and second soak liquid (95). The second soak liquid (95) flows to the cylindrical end (106) of the bowl (102) and can be discharged by gravity. The decanted second soak liquid (95) can be transferred to the mix tank (67). Excess liquid in the mix tank (67) can be transferred to the ethanol production system (4).

As to particular embodiments of the invention, prior to the steps of separation of the soaked particles of corn germ (21) and corn bran (19) from the second soak liquid (94) from the second soak tank (94), the second soak liquid (95) containing particles of corn germ (21) and corn bran (19) can be transferred to a seventh centrifugal force separator (120) with the overflow containing particles of corn germ (21) and corn bran (19) directed to the inlet (71) of an eighth centrifugal force separator (121) each of which operates in the similar manner to the first centrifugal force separator (70) and the second centrifugal force separator (78), as above-described. Operation of the seventh and eighth centrifugal force separators (120) (121) separates the relatively lighter particles of germ (21) (and other lighter particles such as bran particles (19)) to discharge through a first outlet (74) of the seventh and eighth centrifugal force separators (120) (121) (also referred to as the "seventh and eighth centrifugal force separator over flow") (122). The remaining second soak liquid (95) in which the relatively heavier particles of endosperm (20) are suspended can be discharged through a second outlet (75) of the seventh and eighth centrifugal force separators (120) (121) located proximate or at the respective apexes of the conical portion (76) of the cylindrical-conical chamber (73) (also referred to as the "seventh and eighth centrifugal force separator under flow") (123). The overflow (122) can be directed to a third liquid separator (124) in the form of a gravity screen (86), as above described. The underflow (123) can be directed to a collection tank (109) or directly to an ethanol production system (4) or can be directed to the second soak tank (94) as part of the second soak liquid (95). The germ (21) and the bran (19) collected in the third liquid separator (124) can be washed with an amount of wash water (125) from which the carbon dioxide can be scrubbed. The wash water (125) can be directed to the second soak tank (94) to make up part of the second soak liquid (95). The resulting washed germ (21) and bran (19) can be transferred to the decanter (96) and processed as above described.

Again referring primarily to FIG. 5, the resulting dewatered germ (21) and bran (19) can be transferred to the dryer (83) to lower moisture. The dryer (83) can be any of a numerous and varied constructional form such as a rotary steam tube or fluid bed drier. The moisture content of the germ particles after drying can be less than about 10% wt./wt., or can be less than about 5% wt./wt., or less than about 4% wt./wt. The resulting corn germ (21) can have a starch content of less than about 14% wt./wt., less than about 12% wt./wt., less than about 11% wt./wt. and less than about 10% wt./wt. As to certain embodiments the germ product can have starch content in the range of about 6% wt./wt. and about 8% wt./wt., or even less. The reduction of starch content and reduction in other leachable materials from the germ particles contained in the overflow (79) (80) (90) (112) (122) from each the centrifugal force separators, whether separately or in combination can correspondingly increase the corn oil (22) content of the germ (21). The oil content on a dry matter basis can be increased to about 30%, or about 35%, or about 40%, or about 50%, or about 55%. The PDI can be about 45% or greater.

As to certain embodiments the germ (21) from the second soak, dried as above described, can be passed through one or more screens (107) to obtain a desired particle size(s) and passed through an aspirator (108) to remove any residual particles of corn bran (19).

Now referring primarily to FIG. 5 and Table 5, the endosperm fraction (20) generated by the inventive dry-wet corn fractionation system (26) can be coupled to a various configurations of an ethanol production process (4) to increase the amount of ethanol (5) produced, reduce the amount of thermal energy (11) used per unit of ethanol (5) produced, or reduce the cost per unit of ethanol (5) produced. Embodiments of suitable configurations of the ethanol production process (4) which can be coupled to the endosperm fraction (14) generated by the inventive dry-wet corn fractionation system (26) are described for example by Patent Cooperation Treaty Application No. PCT/US2006/045193, hereby incorporated by reference.

Now referring primarily to FIG. 5 and Table 7, the milled germ analysis for three samples of corn germ fraction (16) are shown (Sample A, Sample B, and Sample C) in Section A. Section B of Table 7, presents the results obtained using embodiments of the invention which show decreasing endosperm (21) (AOAC starch %) in processed corn germ (21) and increasing oil % as a function of the duration of the period of time in the first soak liquid (85). Similarly, Section C of Table 7, presents the results obtained using embodiments of the invention which show the decrease in endosperm (21) (AOAC starch %) in processed bran (19) resulting from a 12 hour duration in the period of time the first soak liquid (85).

TABLE 5

|  | Ash | Protein | Crude Fat | Crude Fiber | Starch | Moisture |
|---|---|---|---|---|---|---|
| Dry Milled Germ (16) feedstock | 5.07 | 14.89 | 18.97 | 5.64 | 34.45 | 13.7 |
| $1^{st}$ Pass Hydrocyclone (Overs) Germ | 6.45 | 18.25 | 30.86 | 8.3 | 6.28 | 0 |
| $1^{st}$ Pass Hydrocyclone (Unders) Grits | 0.74 | 9.02 | 2.87 | 3.54 | 60.43 | 0 |
| $2^{nd}$ Pass Hydrocyclone (Overs) Germ | 7.04 | 19.91 | 32.65 | 7.86 | 5.87 | 0 |
| $2^{nd}$ Pass Hydrocyclone (Unders) Grits | 0.69 | 9.05 | 0.96 | 1.1 | 64.21 | 0 |
| $3^{rd}$ Pass Hydrocyclone (Overs) Germ | 6.27 | 19.95 | 32.78 | 8.22 | 5.12 | 0 |
| $3^{rd}$ Pass Hydrocyclone (Unders) Grits | 0.71 | 9.02 | 3.01 | 3.03 | 61.82 | 0 |
| $4^{th}$ Pass Hydrocyclone (Overs) Germ | 6.16 | 19.89 | 32.99 | 6.86 | 5.09 | 0 |
| $4^{th}$ Pass Hydrocyclone (Unders) Grits | 0.61 | 8.97 | 1.12 | 1.23 | 64.88 | 0 |

Note:
most of the endosperm (21)(grits) is removed by the first hydrocyclone (70) and second hydrocyclone (78) pass by mixing at a ratio 1:2 (feedstock:H20). A further reduction in endosperm is evidenced by a pass through a third hydrocyclone (89) and a fourth hydrocyclone (92).

Now referring primarily to FIG. 5 and Table 6, which shows the results of an corn endosperm fraction (14) of a dry mill process (26) (referred to in Table 6 as a dry milled standard meal −18 W: +40 W) processed in accordance with the inventive dry-wet mill fractionation system. The resulting corn endosperm (20) of the first centrifugal force separator under flow (77), the second centrifugal force separator underflow (81), the third centrifugal force separator under flow (91) and the fourth centrifugal force separator under flow (110) can separately or in combination be directed to the ethanol production system (4). The corn endosperm (20) can have a substantially reduced percent crude fat wt./wt. as compared with the conventional dry mill corn endosperm stream. For example the percent crude fat can be less than about 2.5% wt./wt., less than about 2.0% wt./wt., less than about 1.9% wt./wt., and less than 1.5%, or even less. Correspondingly, the corn germ (21) in the over flow (79) (80) (90) (93) from each successive centrifugal force separator (70) (78) (89) (92) increases in percentage crude fat.

TABLE 7

GERM WET MILLING PROCESS ANALYSIS

A. Milled Germ Analysis

| Dry Milled Germ Samples | AOAC* Starch % | Neutral Detergent Fiber % | Fat (Oil) % Ether Extracted |
|---|---|---|---|
| Sample A | 26.17% | 16.23% | 24.83% |
| Sample B | 30.14% | 17.17% | 23.70% |
| Sample C | 31.35% | 17.56% | 22.97% |
| Sample Average | 29.25% | 16.97% | 23.88% |

*AOAC refers to Association of Official Agricultural Chemists official method 948.02 Starch in Plants.

B. Milled Germ Time Soak Analysis

| Dry Milled Germ Samples | AOAC Starch % | Fat (Oil) % Ether Extracted | Soak Time in Hours |
|---|---|---|---|
| Sample A | 6.88% | 44.45% | 4 hrs |

TABLE 6

|  | Ash | Protein | Crude Fat | Crude Fiber | Starch | Moisture |
|---|---|---|---|---|---|---|
| Dry Milled Standard Meal −18 W:+40 W | 2.95 | 13.74 | 5.89 | 6.13 | 56.63 | 20.8 |
| 1st Pass Hydrocyclone (Overs) Germ | 2.14 | 15.09 | 18.11 | 8.3 | 12.67 | 0 |
| 1st Pass Hydrocyclone (Unders) Grits | 1.98 | 10.86 | 2.47 | 10.13 | 58.91 | 0 |
| 2nd Pass Hydrocyclone (Overs) Germ | 2.02 | 16.56 | 22.31 | 7.62 | 9.88 | 0 |
| 2nd Pass Hydrocyclone (Unders) Grits | 1.79 | 9.05 | 2.13 | 9.75 | 58.66 | 0 |
| 3rd Pass Hydrocyclone (Overs) Germ | 1.84 | 16.71 | 22.88 | 13.54 | 8.01 | 0 |
| 3rd Pass Hydrocyclone (Unders) Grits | 1.66 | 9.02 | 1.9 | 3.03 | 59.03 | 0 |
| 4th Pass Hydrocyclone (Overs) Germ | 1.79 | 16.88 | 23.61 | 13.36 | 7.37 | 0 |
| 4th Pass Hydrocyclone (Unders) Grits | 1.61 | 8.76 | 1.54 | 3.21 | 59.45 | 0 |

TABLE 7-continued

GERM WET MILLING PROCESS ANALYSIS

| Sample B | 7.12% | 42.21% | 4 hrs |
|---|---|---|---|
| Sample C | 6.93% | 43.03% | 4 hrs |
| Sample Average | 6.98% | 43.23% | 4 hrs |
| Sample A | 3.97% | 48.12% | 6 hrs |
| Sample B | 4.49% | 47.77% | 6 hrs |
| Sample C | 4.27% | 47.31% | 6 hrs |
| Sample Average | 4.24% | 47.73% | 6 hrs |
| Sample A | 2.62% | 49.36% | 8 hrs |
| Sample B | 3.33% | 48.89% | 8 hrs |
| Sample C | 3.18% | 47.97% | 8 hrs |
| Sample Average | 3.04% | 48.74% | 8 hrs |
| Sample A | 2.41% | 49.46% | 10 hrs |
| Sample B | 2.81% | 50% | 10 hrs |
| Sample C | 2.88% | 48.22% | 10 hrs |
| Sample Average | 2.70% | 49.23% | 10 hrs |
| Sample A | 1.88% | 51.11% | 12 hrs |
| Sample B | 2.17% | 50.68% | 12 hrs |
| Sample C | 2.22% | 50.33% | 12 hrs |
| Sample Average | 2.09% | 50.71% | 12 hrs |

C. Corn Bran (Fiber) From Germ

| AOAC Starch % and NDF % Analysis | AOAC Starch % | Fat (Oil) % Ether Extracted | Neutral Detergent Fiber % | Time (Hours) |
|---|---|---|---|---|
| Samples A, B, & C Average | 29.25% | 23.88% | 16.97% | 0 hrs |
| Samples A, B, & C Average | 4.21% | 1.88% | 61.25% | 12 hrs |

EXAMPLE 1

Germ Wet Milling of Dry Milled Corn Germ

A broad object of embodiments of the invention is to process less than about 20% wt./wt. of the entire grain kernel. As compared to conventional wet milling processes which process the whole or ground grain kernels, wet processing of the dry mill germ of grain resulting from the above described dry mill processes or other conventional dry mill processes confers the advantages of wet mill processing a much reduced weight of material which can achieve and overall cost savings, but additionally provides the advantage of producing a similar or better germ (21) quality (maximum amount of starch content on a dry mass basis of 10% wt./wt. and containing a minimum of 40% oil on dry mass basis wt./wt.) with significantly reduced soak periods. Moreover, germ resulting from embodiments of the invention and from the exemplary process described below can be further processed to extract food-grade oil.

In one exemplary process in accordance with embodiments of the invention, one thousand pounds of large particle corn germ fraction (16) from a dry mill process was processed utilizing an embodiment of the inventive wet mill process (18). The size of the corn germ fraction (16) was estimated as being caught on a US standard screen, size 8. No visual sign of foreign materials, such a weed seeds, stalks, or cobs, was evident. The corn germ fraction (16) was higher in starch content (29.25. % starch wt./wt.) as compared to prior trials would be typical of a corn germ fraction (16) being about 30% starch wt./wt. or less.

Now referring primarily to FIG. 5, the germ was combined with an amount of water (116) (soak liquid (84) in the first soak tank (84). The corn germ fraction (16) was soaked for less than five minutes, and without hydrocyclone (89) (92), separated from the amount of water (116) by gravity screen (82) and reduced in size by Bauer mill (21). The ground corn germ fraction (16) was passed through a two stage hydrocyclone (110) (111) to separate a portion of the grit (endosperm) (20) from a portion of the germ (21) and bran (19).

The overflow (112) containing the germ (21) and the bran (19) was transferred directly to the second soak tank (94) without separation from the first soak liquid (85). The ratio of second soak liquid (95) (water) to dry germ was about 10.0 to 1. The second soak liquid (95) was maintained at a temperature of between about 90° F. and about 170° F. The enzyme (118) alpha amylase (126) was added to the second soak liquid (95) at about 0.01% wt./wt. to aide in starch (endosperm (20)) removal from the germ (21) and bran (19). The germ (21) and the bran (19) was soaked for about 24 hours. To assess oil purity of the germ (21), samples were periodically taken at about 2 hour intervals. Certain results are set out in Table 8.

TABLE 8

Germ Wet Milling Product Starch And Oil Analysis Over Time (dmb)

| | Estimate Average Soak Time (hrs:mins) | Ether Oil Ext | Starch AOAC |
|---|---|---|---|
| Start Material | 0 | 23.88 | 29.25 |
| Germ 1 | 4:04 | 43.51 | 9.1 |
| Germ 2 | 5:31 | 47.43 | 3.9 |
| Germ 3 | 7:33 | 48.74 | 3.2 |
| Germ 4 | 24:00 | 51.86 | 1.6 |

NA = not analyzed.
Germ was aspirated post drying and prior to analysis.

The second soak liquid (95) containing the germ (21) and bran (19) was then passed through a gravity screen (124/86) to separate the second soak liquid (95) from the germ (21) and bran (19). The processed germ (21) and bran (22) were rinsed with wash water (125) in the gravity screen (124/86). The moist germ (21) and bran (19) was then passed to a dryer (83) and the moisture content was reduced to below 12%. The dried processed germ (21) and bran (19) was then separated into three particle size categories by passing through two different sized screens (107). Each particle size category was then passed through an aspirator (108) to separate the bran (19) from the germ (21). The result of each size category was compared to the un-sized, dried bran (19) and germ (21) mix. The results are set out in Table 9. The results show that sizing the processed bran (19) and germ (21) increased the germ yield by about 5.0% by weight.

TABLE 9

The Affect Of Sizing Germ And Bran Prior To Aspiration (%).

| | Germ | Germ Tip Cap and Bran |
|---|---|---|
| Sized | 97.0 | 7.0 |
| Not Sized | 92.0 | 12.0 |

The under flow (113) from the two stage hydroclone (110) (111) was passed through a dewatering screen to separate the grits (20) (corn endosperm) from first soak liquid (85). The grits (20) were not further processed as the two stage hydroclone (110) (11) produced an excellent quality grit (20) essentially free of germ (21) and bran (19).

The mass balance splits of the dry milled germ after being processed by the instant embodiment of the invention was determined. The dry milled germ used in this example had an initial moisture of about 12.5%, therefore the resulting mass balance values in pounds for the grits (20), germ (21) and bran (19) resulting from the exemplary process are presented in Table 10 on an 12.5% moisture basis. The slurry solids (127) contained in the soak liquids (85) (95) were calculated by difference.

TABLE 10

The Mass Balance Splits Of Dry Milled Germ

|  | Weight, lbs (12.5% Moisture Basis) | Yield (12.5% Moist Basis) |
|---|---|---|
| Starting Material | 1000.0 | NA |
| Clean Germ (Not Aspirated) | 354 | 35.4% |
| Grits - Screened | 410 | 41.0% |
| Slurry Nutrients | 236* | 23.6% |

*Estimated by difference

The bran starch content on a dry mass basis wt./wt. on the bran (19) separated by aspiration (108) was also determined and the results are presented in Table 11.

TABLE 11

Affect Of Germ Wet Milling On Bran Starch Content (dmb, w/w).

|  | AOAC Starch, % | NDF, % | Average Soak Time (hrs) |
|---|---|---|---|
| Dry Frac Starting Material | 29.25 | NA | 0 |
| Bran | 4.21 | 61.25 | 24.0 |

The bran starch content achieved by the instant exemplary process is about 4.21%. The bran starch content of various conventional dry mill process bran can be greater than 16% wt./wt. on a dry mass basis. The use of conventional dry mill bran polishing can reduce the bran starch content to between about 5% and about 16% wt./wt. on a dry mass basis. The reduction of the bran starch content much below that achieved with the exemplary process would be difficult. Prior trials involving longer soak times or higher soak temperatures did not achieve further reduce the bran starch content. The bran (19) resulting from this exemplary process was a high quality food grade bran due to the low starch content and the high neutral-detergent fiber. Additionally, embodiments of this inventive process do not utilize sulfur dioxide in the soak steps as compared to conventional wet mill processes, accordingly the resulting bran (19) produced by embodiments of the invention does not include this contaminant.

In summary, the exemplary wet mill process demonstrates that the soak time can be substantially reduced in processing dry mill germ fraction as compared to conventional wet mill processes and still achieve a similar or greater germ quality.

As can be easily understood from the foregoing, the basic concepts of the present invention may be embodied in a variety of ways which includes the best mode of the invention. The invention involves numerous and varied dry-wet corn mill devices and methods of wet-dry milling and fractionation of corn. While certain examples are provided in the context of a dry corn mill process (13), it is not intended that these examples limit the use of the invention to corn fractions derived solely from the dry corn mill process (13) described, but rather are intended to be illustrative such that a person of ordinary skill in the art can make and use the invention in the context of the numerous and varied processes that produce corn fractions.

As such, the particular embodiments or elements of the invention disclosed by the description or shown in the figures or tables accompanying this application are not intended to be limiting, but rather exemplary of the numerous and varied embodiments generically encompassed by the invention or equivalents encompassed with respect to any particular element thereof. In addition, the specific description of a single embodiment or element of the invention may not explicitly describe all embodiments or elements possible; many alternatives are implicitly disclosed by the description and figures.

It should be understood that each element of an apparatus or each step of a method may be described by an apparatus term or method term. Such terms can be substituted where desired to make explicit the implicitly broad coverage to which this invention is entitled. As but one example, it should be understood that all steps of a method may be disclosed as an action, a means for taking that action, or as an element which causes that action. Similarly, each element of an apparatus may be disclosed as the physical element or the action which that physical element facilitates. As but one example, the disclosure of a "mill" should be understood to encompass disclosure of the act of "milling"—whether explicitly discussed or not—and, conversely, were there effectively disclosure of the act of "milling", such a disclosure should be understood to encompass disclosure of a "mill" and even a "means for milling." Such alternative terms for each element or step are to be understood to be explicitly included in the description.

In addition, as to each term used it should be understood that unless its utilization in this application is inconsistent with such interpretation, common dictionary definitions should be understood to included in the description for each term as contained in the Random House Webster's Unabridged Dictionary, second edition, each definition hereby incorporated by reference.

Thus, the applicant(s) should be understood to claim at least: i) each of the dry-wet corn mill systems herein disclosed and described, ii) the related methods disclosed and described, iii) similar, equivalent, and even implicit variations of each of these devices and methods, iv) those alternative embodiments which accomplish each of the functions shown, disclosed, or described, v) those alternative designs and methods which accomplish each of the functions shown as are implicit to accomplish that which is disclosed and described, vi) each feature, component, and step shown as separate and independent inventions, vii) the applications enhanced by the various systems or components disclosed, viii) the resulting products produced by such systems or components, ix) methods and apparatuses substantially as described hereinbefore and with reference to any of the accompanying examples, x) the various combinations and permutations of each of the previous elements disclosed.

The background section of this patent application provides a statement of the field of endeavor to which the invention pertains. This section may also incorporate or contain paraphrasing of certain United States patents, patent applications, publications, or subject matter of the claimed invention useful in relating information, problems, or concerns about the state of technology to which the invention is drawn toward. It is not intended that any United States patent, patent application, publication, statement or other information cited or incorporated herein be interpreted, construed or deemed to be admitted as prior art with respect to the invention.

The claims set forth in this specification are hereby incorporated by reference as part of this description of the invention, and the applicant expressly reserves the right to use all of or a portion of such incorporated content of such claims as additional description to support any of or all of the claims or any element or component thereof, and the applicant further expressly reserves the right to move any portion of or all of the incorporated content of such claims or any element or component thereof from the description into the claims or viceversa as necessary to define the matter for which protection is sought by this application or by any subsequent application or continuation, division, or continuation-in-part application thereof, or to obtain any benefit of, reduction in fees pursuant to, or to comply with the patent laws, rules, or regulations of any country or treaty, and such content incorporated by reference shall survive during the entire pendency of this application including any subsequent continuation, division, or continuation-in-part application thereof or any reissue or extension thereon.

The claims set forth below, if any, are intended to describe the metes and bounds of a limited number of the preferred embodiments of the invention and are not to be construed as the broadest embodiment of the invention or a complete listing of embodiments of the invention that may be claimed. The applicant does not waive any right to develop further claims based upon the description set forth above as a part of any continuation, division, or continuation-in-part, or similar application.

I claim:

1. The method of processing a grain fraction, comprising the steps of:
    obtaining a grain fraction including an amount of endosperm and at least one of an amount of bran or an amount of germ;
    combining said dry grain fraction with an amount of mix liquid;
    generating a first rotational flow in said grain fraction combined with said amount of mix liquid, said rotational flow having an upper portion and a lower portion;
    distributing said amount of endosperm toward said lower portion of said first rotational flow and said at least one of said amount of bran or said amount of germ toward said upper portion of said rotational flow;
    discharging said upper portion of said first rotational flow containing said at least one of said amount of bran or said amount of germ as a first overflow; and
    discharging said lower portion of said first rotational flow containing said amount of endosperm as a first underflow.

2. The method of processing a grain fraction as described in claim 1, further comprising the step of separating said at least one of said amount of bran or said amount of germ from said first overflow.

3. The method of processing a grain fraction as described in claim 2, further comprising the steps of:
    generating a second rotational flow in said first under flow;
    discharging said upper portion of said second rotational flow containing said at least one of said amount of bran or said amount of germ as a second overflow; and
    discharging said lower portion of said second rotational flow containing said amount of endosperm as a second underflow.

4. The method of processing a grain fraction as described in claim 3, separating said at least one of said amount of bran or said amount of germ from said second overflow.

5. The method of processing a grain fraction as described in claim 4, transferring an amount of first soak liquid to one or a combination of said first overflow and said second overflow.

6. The method of processing a grain fraction as described in claim 5, soaking said at least one of said amount of bran or said amount of germ in one or the combination of said first overflow and said second overflow.

7. The method of processing a grain fraction as described in claim 6, further comprising the step of separating said at least one of said amount of bran or said amount of germ from said first soak liquid.

8. The method of processing a grain fraction as described in claim 7, further comprising comminuting said at least one of said amount of bran or said amount of germ separated from said first soak liquid.

9. The method of processing a grain fraction as described in claim 8, further comprising the step of recombining said at least one of said amount of bran or said amount of germ comminuted with said first soak liquid.

10. The method of processing a grain fraction as described in claim 9, further comprising the steps of:
    generating prior to separating said at least one of said amount of bran or said amount of germ from said first soak liquid a third rotational flow in said grain fraction combined with said amount of soak liquid, said third rotational flow having an upper portion and a lower portion;
    distributing said amount of endosperm toward said lower portion of said third rotational flow and said at least one of said amount of bran or said amount of germ toward said lower portion of said rotational flow;
    discharging said upper portion of said third rotational flow containing said at least one of said amount of bran or said amount of germ as a third overflow; and
    discharging said lower portion of said third rotational flow containing said amount of endosperm as a third underflow.

11. The method of processing a grain fraction as described in claim 10, further comprising the steps of:
    generating a fourth rotational flow in said third under flow;
    discharging said upper portion of said fourth rotational flow containing said at least one of said amount of bran or said amount of germ as a fourth overflow; and
    discharging said lower portion of said fourth rotational flow containing said amount of endosperm as a fourth underflow.

12. The method of processing a grain fraction as described in claim 11, transferring an amount of second soak liquid to one or both of said third overflow and said fourth overflow.

13. The method of processing a grain fraction as described in claim 12, soaking said at least one of said amount of bran or said amount of germ of one or both of said third overflow and said fourth overflow in said second soak liquid.

14. The method of processing a grain fraction as described in claim 13, further comprising the step of separating said at least said at least one of said amount of bran or said amount of germ from said amount of second soak liquid.

15. The method of processing a grain fraction as described in claim 14, further comprising the step of combining said second soak liquid in said first soak tank.

16. The method of processing a grain fraction as described in claim 14, further comprising the steps of:
    generating prior to transferring an amount of second soak liquid to one or both of said third overflow and said fourth overflow a fifth rotational flow in comminuted at least one of said amount of bran and said amount of germ combined with said amount of soak liquid, said fifth rotational flow having an upper portion and a lower portion;
    distributing said amount of endosperm toward said lower portion of said fifth rotational flow and said at least one of said amount of bran or said amount of germ toward said upper portion of said rotational flow;
    discharging said upper portion of said fifth rotational flow containing said at least one of said amount of bran or said amount of germ as a fifth overflow; and discharging said lower portion of said fifth rotational flow containing said amount of endosperm as a fifth underflow.

17. The method of processing a grain fraction as described in claim 16, further comprising the steps of:
generating a sixth rotational flow in said fifth under flow;
discharging said upper portion of said sixth rotational flow containing said at least one of said amount of bran or said amount of germ as a sixth overflow; and
discharging said lower portion of said fourth rotational flow containing said amount of endosperm as a sixth underflow.

18. A method of processing a grain fraction as described in claim 17, further comprising the steps of:
generating a seventh rotational flow in comminuted soaked at least one of said amount of bran and said amount of germ combined with said amount of second soak liquid, said seventh rotational flow having an upper portion and a lower portion;
distributing said amount of endosperm toward said lower portion of said seventh rotational flow and said at least one of said amount of bran or said amount of germ toward said upper portion of said seventh rotational flow;
discharging said upper portion of said seventh rotational flow containing said at least one of said amount of bran or said amount of germ as a seventh overflow; and
discharging said lower portion of said seventh rotational flow containing said amount of endosperm as a seventh underflow.

19. The method of processing a grain fraction as described in claim 18, further comprising the steps of:
generating an eight rotational flow in said seventh under flow;
discharging said upper portion of said eighth rotational flow containing said at least one of said amount of bran or said amount of germ as an eighth overflow; and
discharging said lower portion of said eighth rotational flow containing said amount of endosperm as a eighth underflow.

20. The method of processing a grain fraction as described in claim 19, further comprising the steps of separating said second soak liquid from said eighth overflow; and delivering said at least one of said amount of bran and said amount of germ to a decantor.

* * * * *